United States Patent
Wyand et al.

(10) Patent No.: US 10,828,360 B1
(45) Date of Patent: Nov. 10, 2020

(54) METHODS FOR INHIBITING BIOFILM FORMATION

(71) Applicant: ONEBIOPHARMA INC., Boston, MA (US)

(72) Inventors: Michael Wyand, Boston, MA (US); John Donnelly, Boston, MA (US); Gerald F. Swiss, San Diego, CA (US)

(73) Assignee: OneBioPharma, Inc., Boston, MA (US)

( * ) Notice: Subject to any disclaimer, the term of this patent is extended or adjusted under 35 U.S.C. 154(b) by 0 days.

(21) Appl. No.: 16/577,955

(22) Filed: Feb. 4, 2020

(51) Int. Cl.
*A61K 39/02* (2006.01)
*A61K 39/08* (2006.01)

(52) U.S. Cl.
CPC .............. *A61K 39/08* (2013.01); *A61K 39/02* (2013.01)

(58) Field of Classification Search
None
See application file for complete search history.

(56) References Cited

U.S. PATENT DOCUMENTS

| | | | |
|---|---|---|---|
| 5,646,123 | A | 7/1997 | Ippolito et al. |
| 7,786,255 | B2 | 8/2010 | Pier et al. |
| 8,492,364 | B2 | 7/2013 | Pier et al. |
| 2005/0118198 | A1 | 6/2005 | Pier et al. |

OTHER PUBLICATIONS

"Biofilm." *Wikipedia: The Free Encyclopedia*. Wikimedia Foundation, Inc. Nov. 25, 2019. Web. Dec. 11, 2019. 24 pages. <en.wikipedia.org/wiki/Biofilm>.
Little, D.J. et al. (Sep. 11, 2015, e-published Jul. 22, 2015). "The Protein BpsB Is a Poly-$\beta$-1,6-N-acetyl-d-glucosamine Deacetylase Required for Biofilm Formation in *Bordetella bronchiseptica*," *J. Biol. Chem.* 290(37):22827-22840. Web. Dec. 6, 2019.
UniProt Protein Database, accession Q6TYB1; Q54067, "Poly-beta-1,6-N-acetyl-D-glucosamine N-deacetylase," Mar. 15, 2005, Entry version 63 (Nov. 13, 2019), retrieved from http://www.uniprot.org/uniprot/Q6TYB1. Retrieved Dec. 11, 2019. 2 pages.
U.S. Appl. No. 16/823,290, filed Mar. 18, 2020, Michael Wyand.
U.S. Appl. No. 62/892,400, filed Aug. 27, 2019, Rebecca Dabora et al.
U.S. Appl. No. 62/939,331, filed Nov. 22, 2019, Michael Wyand et al.
U.S. Appl. No. 62/994,130, filed Mar. 24, 2020, Michael Wyand et al.
Gening, M.L., et al. (2010). "Synthetic $\beta$-(1→6)-Linked N-Acetylated and Nonacetylated Oligoglucosamines Used to Produce Conjugate Vaccines for Bacterial Pathogens." *Infection and Immunity*. 78(2): 764-772.
Gening, M.L., et al. (2013, e-published Apr. 28, 2013). "Linear and cyclic oligo-$\beta$-(1→6)-D-glucosamines: Synthesis, conformations, and applications for design of a vaccine and oligodentate glycoconjugates." *Pure Appl. Chem.* 85(9):1879-1891.

*Primary Examiner* — Padmavathi Baskar
(74) *Attorney, Agent, or Firm* — Mintz Levin Cohn Ferris Glovsky & Popeo

(57) ABSTRACT

Disclosed are methods and kits of parts useful in inhibiting biofilm formation in vivo in subjects at risk of developing biofilms. These methods include inhibiting biofilm formation where the extracellular matrix in the biofilm includes poly-$\beta$-(1→6)glucosamine structures.

7 Claims, 2 Drawing Sheets

Figure 1: Typical ¹H NMR Spectrum of the Penta Dimer
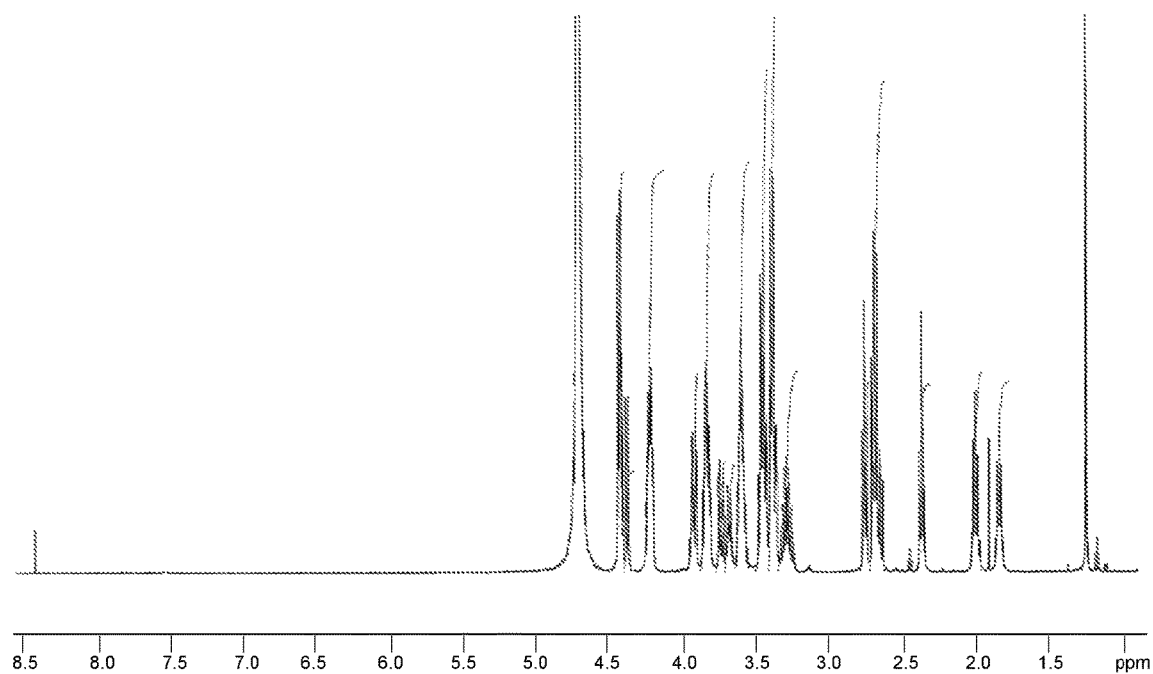

Figure 2: Typical $^{13}$C NMR Spectrum of the Penta Dimer
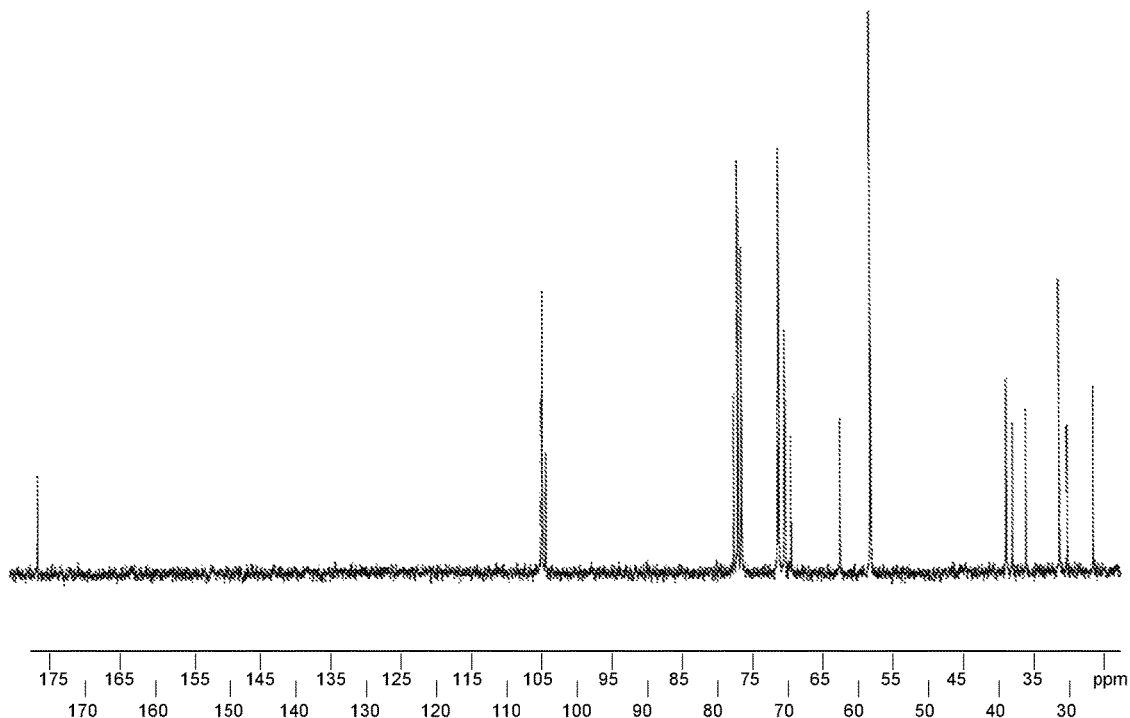

METHODS FOR INHIBITING BIOFILM FORMATION

BACKGROUND

Field of the Invention

This disclosure relates to methods and kit of parts useful in inhibiting in vivo biofilm formation in subjects at risk of developing biofilms. These methods include inhibiting biofilm formation where oligo- and/or poly-β-(1→6)glucosamine structures are an essential component of biofilms.

State of the Art

Many motile (planktonic) bacteria comprise polysaccharides in their cell wall including, in many cases, poly-(N-acetyl)-beta-(1→6)-glucosamine (PNAG) wherein a portion of the N-acetyl groups are deacetylated by endogenous enzymes. During biofilm formation, there is an increased expression of PNAG coupled with transcription by a different set of genes. The amount of deacetylated PNAG also increases during biofilm formation phase but at a rate that is believed to be disproportionately high compared to the amount in the motile phase.

It has been reported that the expression of deacetylase enzymes targeting poly-(N-acetyl)-β-(1→6)-glucosamine is an essential component in the formation of biofilms. See, e.g., Little, et al., JBC, Jul. 22, 2015 (available on the worldwide web at www.jbc.org/content/early/2015/07/22/jbc.M115.672469.full.pdf). This increase would explain the substantially impermeable nature of the extracellular matrix as protonated amino groups ($-NH_3^+$) arising after deacetylation can pair with carboxylate groups found in the protein that also makes up the biofilm. See, e.g., the worldwide web at www.uniprot.org/uniprot/Q6TYB1 This ionic pairing would occur between the protonated amino groups of the polysaccharide and the carboxylate groups ($CO_2^-$) of the protein (e.g., side chains of glutamic acid or aspartic acid). In addition, the polysaccharide and the protein components of the biofilm can participate in hydrophilic bonding, hydrogen bonding, and other bonding mechanisms to drive the impermeable nature of the biofilm.

Biofilms are a major concern with subjects having implants such as pacemakers, breast augmentation, prosthesis (including hip and knee replacements), and multiple other devices that are implanted into the body. In addition, many diseases such as cystic fibrosis, periodontitis, and osteomyelitis involve biofilms. It is estimated that about 80% of all bacterial infections are associated with biofilms. See, e.g., the worldwide web at en.wikipedia.org/wiki/Biofilm. Moreover, treatment of these infections is exceptional difficult as the nearly impermeable nature of the biofilm inhibits immune components and antibiotics from penetrating into the bacteria under the biofilm. As such, it would be particularly beneficial to prevent formation of these biofilms.

SUMMARY

Vaccines for treating or preventing infections using poly β-(1→6)-glucosamine attached via a linker to tetanus toxoid have been developed, for example as described in U.S. Pat. No. 7,786,255, which is incorporated herein by reference in its entirety. These vaccines are disclosed to inhibit infections involving PNAG expressing microbes, including bacteria, fungi, and the like.

This disclosure is directed, in part, to methods for inhibiting biofilm formation in subjects at risk of such formation. Given that, once formed, biofilms are generally impervious to treatment, preventing biofilm formation is considered the best approach to deal with this condition. Many, if not most, of the bacteria that create biofilms express poly-(N-acetyl)-β-(1→6)-glucosamine in their cell wall. Moreover, the transition of a bacterial population from their motile phase to their biofilm formation phase results in expression of PNAG from a different set of genes in the bacterial genome, suggesting that such expression may also result in expression or an increased expression of one or more deacetylase enzymes.

Without being limited to any theory, this transition results in an increase in expression of PNAG coupled with what is believed to be a disproportionate increase in the amount of deacetylated N-acetyl groups. This latter characteristic would enhance the reactivity of these polysaccharides with protein components found in the biofilm by increasing the number of reactive amino ($-NH_2$) arising from deacetylation and consequently the number of protonated amino groups ($-NH_3^+$). Ionic pairing results from these cationic protonated amino groups with carboxylate groups of aspartic/glutamic acid residues found in protein incorporated in the biofilm increases the strength of the resulting biofilm.

PNAG vaccines as described herein that comprise oligo-deacetylated β-(1→6)-glucosamine structure generate polyclonal antibodies in vivo, including those that target deacetylated portions of PNAG. As the bacterium transitions from a motile phase to a biofilm-forming phase, the amount of deacetylated β-(1→6)-glucosamine structures in the cell wall increases. Hence, those antibodies targeting oligo-deacetylated β-(1→6)-glucosamine structures are particularly suited to bind to and then destroy such transitioning bacteria, thereby preventing these bacteria from generating a biofilm. Such, in turn, allows for prophylactic treatment of subjects at risk of biofilm formation by administration of the vaccine prior to onset of that risk.

Accordingly, provided herein is a method for inhibiting biofilm formation in a subject at risk of biofilm formation including those who are scheduled to undergo implant surgery. In an embodiment, there is provided a method for inhibiting biofilm formation in such subjects which method comprises:
  a) selecting an immune competent subject scheduled for implant surgery; and
  b) administering to said subject prior to surgery an effective amount of a vaccine so as to generate polyclonal antibodies in vivo against oligo-β-(1→6)-glucosamine structures;
  wherein said antibodies are generated prior to implantation surgery so as inhibit formation of biofilm formation in said subject subsequent to said surgery.

In another embodiment, a subject is identified who is at risk of biofilm formation, such as those who are at risk of contracting a disease that involves biofilm formation. Such diseases include by way of example only, cystic fibrosis, periodontitis, and osteomyelitis. In an embodiment, a method is provided for inhibiting biofilm formation in such subjects which method comprises:
  a) selecting an immune competent subject at risk of acquiring biofilm formation due to being at risk of cystic fibrosis, periodontitis or osteomyelitis;
  b) administering to said subject an effective amount of a vaccine so as to generate polyclonal antibodies in vivo against oligo-β-(1→6)-glucosamine structures, wherein said antibodies are generated prior to contracting said disease so as to inhibit biofilm formation if the subject acquires one of these diseases.

In one embodiment, the methods employ a vaccine comprising oligomeric β-(1→6)-glucosamine-linked groups bound to a protein toxoid.

In one embodiment, the oligomeric β-(1→6)-glucosamine-linked groups bound to a protein toxoid comprises a loading level of at least 10 and, preferably, at least 25 and, more preferably, from about 31 to 39 oligomeric β-(1→6)-glucosamine-linked groups onto tetanus toxoid. In one embodiment, the protein toxoid has from at least 25 and preferably at least 31 reactive amino functionalities.

In another preferred embodiment, the toxoid component in the vaccine comprises tetanus toxoid and, more preferably, a tetanus toxoid having at least 85 percent of the toxoid in monomeric form. In one embodiment, the toxoid component in the vaccine comprises at least 90 percent of the toxoid in monomeric form. In some embodiments, the toxoid includes at least 90 percent to 99.9 percent of the toxoid in monomeric form, and preferably at least 95 percent to 99.9 percent of the toxoid in monomeric form, or any subvalue or subrange there between.

In one embodiment, the amount of low molecular weight reactive amino compounds in the vaccine is no more than 3 weight percent relative to the weight of toxoid present. In another embodiment, the amount of low molecular weight amino compounds in the composition is less than 2 weight percent and preferably less than 1 weight percent based on the weight of the toxoid present, and even more preferably less than 0.5 weight percent based on the weight of the toxoid present. In another preferred embodiment, the amount of monomer is over 99 area percent, for example, based on HPLC.

Accordingly, in one preferred embodiment, the methods employ a vaccine that comprises at least 25 and preferably from about 31 to about 39 oligomeric-β-(1→6)-glucosamine groups linked units onto a tetanus toxoid carrier via a linker wherein the oligomer comprises from 3 to 12 repeating β-(1→6)-glucosamine units and further wherein said tetanus toxoid comprises at least 25 and preferably at least 31 reactive amino functionalities and at least 85 percent of the toxoid components are in monomeric form, or in some embodiments, at least 90%. Such vaccines provide effective immunity to a subject against biofilm formation.

x represents the loading factor and is an integer from 10 to 40;

y is an integer from 1 to 10;

B is a linker group connecting A to C; and

C is an antigenic carrier.

In one preferred embodiment, x is an integer from 25 to 39 or from 31 to 39 and B is a linker group represented by the formula:

where the left side of the formula is attached to A and the right side is attached to and C.

In one preferred embodiment, the antigenic carrier is a tetanus toxoid carrier that comprises at least 25 reactive amino groups and at least 90 percent by number of the toxoid is in monomeric form.

In one embodiment, the methods provide for a vaccine composition that comprises a pharmaceutically acceptable carrier and an effective amount of any one of the vaccines as described above.

In a preferred embodiment of formula I above, the vaccine used in the methods described herein is represented by formula II:

(A'-B)$_x$—C             II where A' is a penta-β-(1→6)-glucosamine (carbohydrate ligand) group of the formula:

In one embodiment, the methods employ a vaccine represented by formula I:

(A-B)$_x$—C             I where A comprises from 3 to 12 repeating β-(1→6)-glucosamine units or mixtures thereof having the formula:

and B, C and x are as defined above, provided that at least 90 percent by number of the toxoid is in monomeric form, or in some embodiments, at least 95%.

Representative compounds for use as described herein are set forth in the table below:

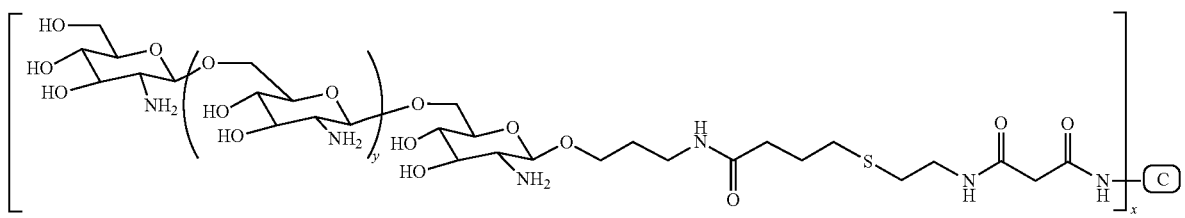

| Example | y | x | Percent monomer |
|---------|----|----|-----------------|
| A | 2 | 31 | 90% |
| B | 3 | 36 | 95% |
| C | 6 | 33 | 95% |
| D | 10 | 29 | >95% |
| E | 3 | 34 | >95% |
| F | 4 | 33 | 90% |
| G | 3 | 37 | >90% |
| H | 3 | 35 | >99% |

In one embodiment, the vaccines used in the methods described herein employ a tetanus toxoid monomer that comprises no more than about 3 weight percent of low molecular weight amino groups.

BRIEF DESCRIPTION OF THE DRAWINGS

FIG. 1 illustrates the $^1$H NMR for compound 17 (as described below).

FIG. 2 illustrates the $^{13}$C NMR for compound 17.

DETAILED DESCRIPTION

This disclosure provides for methods for inhibiting biofilm formation. In embodiment, these methods employ vaccines comprising β-(1→6)-glucosamine groups.

Prior to describing the methods in more detail, the following terms will first be defined. If a term used herein is not defined, it has its generally accepted scientific or medical meaning.

The terminology used herein is for the purpose of describing particular embodiments only and is not intended to be limiting. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (−) 10%, 5%, 1%, or any subrange or subvalue there between. Preferably, the term "about" means that the amount may vary by +/−10%.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "β-(1→6)-glucosamine unit" or "glucosamine unit" refers to individual glucosamine structures as follows:

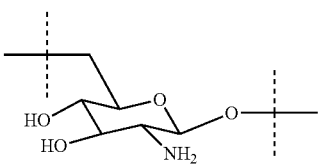

where the 6-hydroxyl group is condensed with the 1 hydroxyl group of the preceding glucosamine unit and where the dashed lines represent binding sites to the preceding and succeeding glucosamine units. When combined with another "β-(1→6)-glucosamine unit, the resulting disaccharide has the structure:

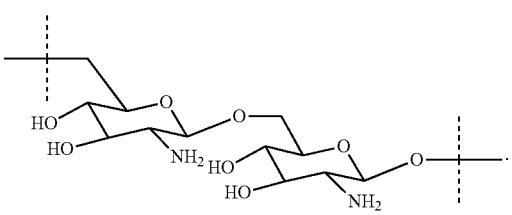

The term "oligosaccharide comprising a β-(1→6)-glucosamine group" refers to that group on the vaccine compound that mimics a portion of the cell wall of pathogenic bacteria which are defined to be "oligosaccharide β-(1→6)-glucosamine structures" (as defined herein). Again, such groups are limited to 3 to 12 β-(1→6)-glucosamine units.

The term "oligosaccharide or polysaccharide comprising N-acetyl β-(1→6)-glucosamine structures" refer to those structures found in the cell wall of microbes. The microbial wall contains a large number of these structures that are conserved across many microbial lines. These structures are found in the microbial cell wall and include those oligosaccharides wherein the majority of their units are N-acetyl β-(1→6)-glucosamine.

The term "vaccine" as used herein refers to vaccines comprising oligosaccharide β-(1→6)-glucosamine groups attached via a linker to an antigen. "Vaccine compositions" refer to vaccines employed in combination with a biocompatible carrier such as a sterile aqueous carrier, an adjuvant, and optionally one more components such as preservatives, antioxidants, buffers, and the like. These compositions are used in methods to inhibit biofilm formation in a subject at risk of such formation. As many bacteria comprise cell walls that have oligo-N-acetyl-β-(1→6)-glucosamine structures which are partially deacetylated, the vaccine compositions used in the methods described herein are capable of providing effective protection against biofilm formation arising from multiple bacterial species. Such microbes include, without limitation, Gram-positive bacteria, Gram-negative bacteria, antibiotic resistant bacteria (e.g., methicillin resistant *Staphylococcus aureus*), fungi, and the like.

The vaccines compounds refer to the compounds of formula I and II. These compounds may exist as solvates, especially hydrates. Hydrates may form during manufacture of the compounds or compositions comprising the compounds, or hydrates may form over time due to the hygroscopic nature of the compounds. Compounds described herein may exist as organic solvates as well, including DMF, ether, and alcohol solvates among others. The identification and preparation of any particular solvate is within the skill of the ordinary artisan of synthetic organic or medicinal chemistry.

"Subject" refers to a mammal. The mammal can be a human or non-human mammal but preferably is a human.

"Inhibit" or "Inhibiting biofilm formation in a subject" and terms similar thereto as used herein refer to the ability of a defined amount of the vaccine composition to generate an antibody response in vivo that is sufficient to 1) reduce the likelihood that a biofilm will form; or 2) inhibit progression of a biofilm or arresting its development both as compared to subjects not treated with the vaccine. In some cases, the methods described herein reduce biofilm formation by 30%, 40% or 50% or more when measured by, for example, the extent of biofilm formed in comparative untreated controls.

"Effective amount" refers to the amount of a vaccine composition that is sufficient to treat the disease or disorder afflicting a subject or to prevent such a disease or disorder from arising in said subject or patient.

"Reactive amino functional group" refers to a primary amino groups (—NH$_2$) that are found on lysine and guanidine side chains of tetanus toxoid but do not include amido (—NHC(O)—) groups found in peptide linkages or amido side chains of tetanus toxoid such as that found in glutamine.

"Implant" refers to any device placed into the body for medical or physical reasons and includes, by way of example only, prosthesis such as joint replacement implants, pace makers, breast augmentation, heart valve implants, and the like.

"Immune competent" refers to subjects who are capable of mounting an immune response to an antigen. In one embodiment, an immune competent subject is one who has a white blood cell (WBC) count of at least about 1000 WBC per microliter, preferably at least about 1500 WBC per microliter, more preferably at least about 2000 WBC per microliter, even more preferably, about 3000 WBC per microliter and, most preferably, about 4000 WBC per microliter.

The term "linker" refers to a divalent biocompatible group comprising from about 1 to about 50 atoms (other than hydrogen) comprising carbon, oxygen, nitrogen, sulfur, phosphorus, silicon, and the like wherein the valences of each atom (except for the divalent linking atoms) are satisfied by hydrogen, carbon, oxygen, nitrogen, sulfur, and the like as is well understood in the art. Such linkers serve to space the oligosaccharide structure (A) from the antigen (C) and which is divalent wherein one functional group is capable of binding to a reciprocal functional group of the antigen and the other functional group is capable of binding to a reciprocal functional group of the oligosaccharide structure.

The term "antigen" as it relates component C of formula I and II refers to a protein structure that induces an antigenic response in a subject including the generation of antibodies. Suitable antigens are well known in the art and include tetanus toxoid, diphtheria toxoid and the like. In some cases, the toxoid forms oligomers which, if desired, can be separated from the monomeric toxoid, for example as per the examples below.

General Synthetic Methods

The vaccines used in the methods described herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, *Protecting Groups in Organic Synthesis*, Third Edition, Wiley, New York, 1999, which is incorporated herein by reference in its entirety, and references cited therein.

The starting materials for the following reactions are generally known compounds or can be prepared by known procedures or obvious modifications thereof. For example, many of the starting materials are available from commercial suppliers such as SigmaAldrich (St. Louis, Mo., USA), Bachem (Torrance, Calif., USA), Emka-Chemce (St. Louis, Mo., USA). Others may be prepared by procedures, or obvious modifications thereof, described in standard reference texts such as *Fieser and Fieser's Reagents for Organic Synthesis*, Volumes 1-15 (John Wiley, and Sons, 1991), *Rodd's Chemistry of Carbon Compounds*, Volumes 1-5, and *Supplementals* (Elsevier Science Publishers, 1989), *Organic Reactions*, Volumes 1-40 (John Wiley, and Sons, 1991), *March's Advanced Organic Chemistry*, (John Wiley, and Sons, 5$^{th}$ Edition, 2001), and *Larock's Comprehensive Organic Transformations* (VCH Publishers Inc., 1989), each of which is incorporated herein by reference in its entirety.

Synthesis of Representative Vaccine Compounds

The general synthesis of the vaccine compounds used in the methods described herein are known in the art and are disclosed in U.S. patent application Ser. Nos. 10/713,790 and 62/892,400 (which application is currently under petition to convert to a utility application) as well as in U.S. Pat. Nos. 7,786,255 and 8,492,364, each of which is incorporated herein by reference in its entirety. The specific linker used as well as the vaccine antigen are for illustrative purposes only and are not limiting.

In the case of the specific vaccine compounds described herein, the β-(1→6)-glucosamine group is limited to from 3 to 12 units. The formation of the linker group is achieved by art recognized synthetic techniques exemplified but not limited to those found in U.S. Pat. No. 8,492,364 (incorporated herein by reference) and the examples below. Other linkers are well known in the art including those set forth in U.S. Pat. No. 5,646,123 which is incorporated herein by reference in its entirety. In one embodiment, a first portion of the aglycon is attached to the reducing β-(1→6)-glucosamine unit which retains a thiol (—SH) group as depicted below in formula III:

III where y is an integer from 2 to 4 and optionally no more than 40% of the amino groups are N-acetyl groups.

The second portion of the linker may be attached to the tetanus toxoid in the following manner as depicted in formula IV.

IV

In this formula, separate parts of tetanus toxoid are depicted by squiggly lines and are only illustrative in nature and are not intended to provide a complete structure of the toxoid. Any disulfide bridge is represented by a single line connecting the parts. For the sake of clarity, only a single second portion of the linker is illustrated whereas there are multiple such second portions covalently attached to amino groups found on the toxoid.

When the first and second portions of the linker are combined under coupling conditions, a thioether linkage is formed. The reaction is conducted in an inert diluent optionally in the presence of a base so as to scavenge the acid generated. The thioether linkage connects the first and second portions of the linker thereby providing for covalent linkage of the tetanus toxoid to the oligosaccharide β-(1→6)-glucosamine group through the combined linker as illustrated below for a vaccine compound where y is as defined herein.

wherein no more than 40% of the amino groups are optionally N-acetyl groups.

It being understood that the number of β-(1→6)-glucosamine group-linker-groups attached to the tentatus toxoid are stoichiometrically controlled so that about 30 to about 38 of such groups are bound to the toxoid thereby providing for the vaccine compounds.

Methods, Utility and Pharmaceutical Compositions

The vaccines described herein are capable of initiating an effective immune response against pathogenic bacteria that form a biofilm. Such bacteria possess PNAG as well as deacetylated PNAG in their cell walls. Without being limited to any theory, the vaccines described herein comprise deacetylated glucoamine units whereas bacterial PNAG oligosaccharide β-(1→6)-glucosamine structures contain increasing segments or regions of deacetylated PNAG as a precursor to biofilm formation. As such, the antibodies generated by the vaccines used herein may target these deacetylated segments resulting in antibody binding and subsequent killing of the bacteria. Moreover, it is contemplated that as the bacteria evolve from a motile phase into a biofilm forming phase, differential gene expression results in increasing the amount of PNAG expressed as well as a disproportionally greater increase in deacetylated PNAG both on a number basis and a percent basis relative to the amount of PNAG itself. As the antibodies are targeting the deacetylated segments of PNAG, the increase in deacetylated segments renders these antibodies more effective thereby inhibiting incipient formation of biofilms.

In the methods, a vaccine composition, as described herein, is administered prophylactically to subjects at risk of biofilm formation arising from bacteria containing PNAG oligosaccharide β-(1→6)-glucosamine structures in their cell walls. Suitable subjects include, by way of example only, subjects scheduled for implant surgeries including but not limited to hip replacement surgery, knee replacement surgery, ankle replacement surgery, catheter insertions including deep vein catheter insertion, pacemaker surgery, and the like. The vaccine is typically administered to an immune competent subject intramuscularly with a suitable adjuvant to enhance the immune response. After the latency period has passed, the subject has acquired natural immunity against such bacteria. Such immune competent subjects have an effective immune system that can generate an immune response to an antigen. Preferably, for the reasons noted above, such subjects have a white blood count of at least 1000, preferably at least about 1500 WBC per microliter, more preferably at least about 2000 WBC per microliter, even more preferably, about 3000 WBC per microliter and, most preferably, about 4000 WBC per microliter.

In another embodiment, the vaccine compositions described herein can be used prophylactically to inhibit formation of biofilms due to genetic diseases such as cystic fibrosis or other diseases such as periodontitis, and osteomyelitis where the presence of biofilms exacerbates treatment. In the case of genetic diseases, subjects who are determined by genetic testing to be at risk of such diseases can be treated prophylactically to inhibit biofilms from forming. In such cases, administration of the vaccine can be conducted as soon as practical after birth. Typically, vaccination occurs prior to biofilm formation and, in some cases, within two months after birth.

The vaccine compositions described herein are typically administered as an injectable sterile aqueous composition that comprise one or more conventional components well known in the art including, by way of example only, adjuvants, stabilizers, preservatives and the like.

Combinations

The vaccine compounds described herein can be used in conjunction with therapeutic compounds or other appropriate agents as deemed suitable by the attending clinician. In selected cases, the vaccine can be concurrently administered with antibiotics for treating a bacterial infection as well as agents that enhance the immune response induced by the vaccine compound and/or composition. In the case of antibiotics, the selection of the appropriate antibiotic or cocktail of antibiotics and the amount to be administered to the subject is well within the skill of the attending physician based on the specifics of the offending bacteria, the extent of bacterial infection, the age, weight, and otherwise relative health of the subject. As is appropriate, the attending physician may co-administer an immune boosting drug or adjuvant in combination with the vaccines described herein.

The vaccine composition may be administered with an adjuvant that potentiates the immune response to the antigen in the subject. Adjuvants include but are not limited to aluminum compounds such as gels, aluminum hydroxide and aluminum phosphate, and Freund's complete or incomplete adjuvant (e.g., in which the antigen is incorporated in the aqueous phase of a stabilized water in paraffin oil emulsion). As is apparent, the paraffin oil can be replaced with other types of oils such as squalene or peanut oil. Other materials with adjuvant properties include BCG (attenuated *Mycobacterium tuberculosis*) calcium phosphate, levamisole, isoprinosine, polyanions (e.g., polyA:U), lentinan, pertusis toxin, lipid A, Saponins, QS-21 and peptides, e.g., muramyl dipeptide, and immuno stimulatory oligonucleotides such as CpG oligonucleotides. Rare earth salts, e.g., lanthanum and cerium, may also be used as adjuvants. The amount of adjuvant used depends on the subject being treated and the particular antigen used and can readily be determined by one skilled in the art.

EXAMPLES

This invention is further understood by reference to the following examples, which are intended to be purely exemplary of this invention. This invention is not limited in scope by the exemplified embodiments, which are intended as illustrations of single aspects of this invention only. Any methods that are functionally equivalent are within the scope of this invention. Various modifications of this invention in addition to those described herein will become apparent to those skilled in the art from the foregoing description and accompanying claims. Such modifications fall within the scope of the appended claims.

The following terms are used herein and have the following meanings. If not defined, the abbreviation has its conventionally recognized definition.

Å=Angstroms
aq.=aqueous
Biotage=Biotage, a division of Dyax Corp., Charlottesville, Va., USA
bp=boiling point
CAD=charged aerosol detector
DCM=dichloromethane
deg=degree
DMSO=dimethylsulfoxide
eq.=equivalents
EtOAc=ethyl acetate
FEP=fluorinated ethylene propylene
g=gram
$H^1$-NMR=proton nuclear magnetic resonance
h=hour HDPE=high density polyethylene
HPLC=high performance liquid chromatography
MeCN=acetonitrile
kg=kilogram
mbar=millibar
MeOH=methanol
mg=milligram
mL=milliliter
mM=millimolar
mmol=millimole
N=Normal
NBS=N-bromosuccinimide
NIS=N-iodosuccinimide
NMT=N-methyltryptamine
PP=polypropylene
qHNMR=quantitative proton nuclear magnetic resonance
RBF=round bottom flask
RO=reverse osmosis
SEC HPLC=size exclusion chromatography HPLC
SIM=secondary ion mass
TCEP=(tris(2-carboxyethyl)phosphine
TLC=thin layer chromatograph
TMSOTf=methanesulfonic acid, 1,1,1-trifluoro-trimethylsilyl ester
TT=tetanus toxoid
µL=microliter
µm=micron
w/w=weight to weight
w/v=weight to volume Example 1—Tetanus Toxoid Preparation Samples of crude tetanus toxoid were concentrated approximately 10-fold and chromatographed on a Superdex® 200 size exclusion column using two different loadings—0.6% and 1.2% of the column bed volume (commercially available from SigmaAldrich, St. Louis Mo., USA). The elution profiles were monitored by A280 absorbance. Six distinct peaks were observed with the purported monomer fraction representing the largest peak area. Pools were created based on analytical SEC HPLC analysis of the individual fractions. The crude tetanus toxoid and each of the individual pools was analyzed by SEC HPLC and the results are summarized in Table 1 below.

TABLE 1

Analytical SEC HPLC Analysis/Quantification of Superdex 200 Pools

| Sample | % Aggregate | % Monomer | % Fragment |
|---|---|---|---|
| Tetanus Toxoid (TT) Concentrated Stock | 4.14% | 58.58% | 37.28% |
| Concentrated TT Monomer Pool | 0.00% | 99.89% | 0.11% |
| Pool 1 | 98.14% | 0.97% | 0.89% |
| Pool 2 | 18.66% | 80.98% | 0.36% |
| Pool 3 | 0.00% | 0.00% | 100.00% |
| Pool 4 | 0.00% | 0.00% | 100.00% |
| Pool 5 | 0.00% | 0.00% | 100.00% |

The monomer pool revealed a single symmetrical peak with an elution volume consistent with monomeric TT (99.9 area %) and no additional peaks detected. Since the column load contained 58.8 area % monomer, this data confirmed the effectiveness of the preparative Superdex purification protocol under these conditions. The remaining fractions from the Superdex 200 column contained mainly larger molecular weight material (Pools 1 & 2) or lower molecular weight species (Pools 3-5) compared to the TT monomer when monitored by SEC HPLC. The mass balance for the overall process was assessed by protein recovery (BCA) and the results are summarized in Table 2.

TABLE 2

Mass Balance from TT Monomer Purification - Formulation Based on Protein Recovery

| Sample | Volume (mL) | Concentration (mg/mL) | Total Protein (mg) | Total Recovery |
|---|---|---|---|---|
| ARMPCT | 60 | 5.7 | 342 | |
| Concentrated TT | 6.6 | 43.1 | 284.5 | 83% |
| Concentrated TT for Prep SEC | 4 | 43.1 | 172.4 | |
| TT Monomer Pool | 40 | 2.2 | 88.0 | 51% |
| Pool 1 | 8.0 | 0.1 | 0.8 | 0% |
| Pool 2 | 28.0 | 0.8 | 22.4 | 13% |
| Pool 3 | 36.0 | 0.9 | 32.4 | 19% |
| Pool 4 | 64.0 | 0.2 | 12.8 | 7% |
| Pool 5 | 18.0 | 0 | 0 | 0% |
| TT Monomer Pool for Form. | 38.0 | 2.2 | 83.6 | |
| Conc. TT Monomer at pH8 | 4.8 | 15.2 | 73.0 | 87% |

Protein recovery from the spin concentration step was 83% with the losses mainly due to removal of smaller molecular weight proteins/peptide contaminants via the filtrate (data not shown). Following purification by preparative Superdex 200 chromatography, yield of the TT-monomer was 51% with the remainder of the protein recovered in the higher molecular weight/aggregate and smaller molecular weight fractions. Finally, the TT-monomer was recovered in 87% yield following buffer exchange into reaction buffer. For this example, the overall process recovery from crude tetanus toxoid to purified/formulated TT-monomer was 35% based on protein recovery.

The stability of purified TT-monomer was assessed following storage at pH 9.0 (4° or −70° C.) or at pH 7.5 (−70° C.) for up to 4 weeks. Specifically, the monomer content (SEC HPLC) and protein concentrations were monitored at weekly intervals. The TT-monomer did not show a significant change in the SEC fingerprint or protein concentration over 4 weeks at 4° C. (pH 9.0) or frozen at −70° C. (pH 7.5 or 9.0). Since this study utilized a limited set of stability indicating methods, the decision was made to purify the TT monomer in advance of each production campaign and to store the purified TT in reaction buffer (50 mM HEPES, pH 8.0) at 4° C. and use it within 7 days of generation.

Example 2—Attachment of SBAP to TT Monomer

Step 1: Preparation of N-BABA:

$H_2N$~~~COOH  →(bromoacetyl bromide)

1

-continued

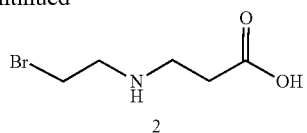

Commercially available beta-alanine, compound 1, is converted to N-BABA (bromoacetyl-β-alanine), compound 2, by reaction with at least a stoichiometric amount of commercially available bromoacetyl bromide. In a first container, β-alanine is combined into water with sodium bicarbonate or other suitable base to scavenge the acid that will be generated during the reaction. The aqueous solution is mixed at about 20±5° C. until a solution is obtained. The solution is then maintained at about 5±5° C. In a separate container, the requisite amount of bromoacetyl bromide is added followed by the addition of dichloromethane. The contents of both containers are combined. After reaction completion, 6N HCl is added and mixed to a pH approximately 2. The resulting N-BABA is extracted from the solution by a suitable solvent such as ethyl acetate. The organic layer is concentrated under conventional conditions such as under vacuum at an elevated temperature such as 60° C. Heptane is then added to precipitate N-BABA that is then collected on a filter and dried in a vacuum oven at 40° C. This product is used as is in the next step.

Step 2: Preparation of SBAP:

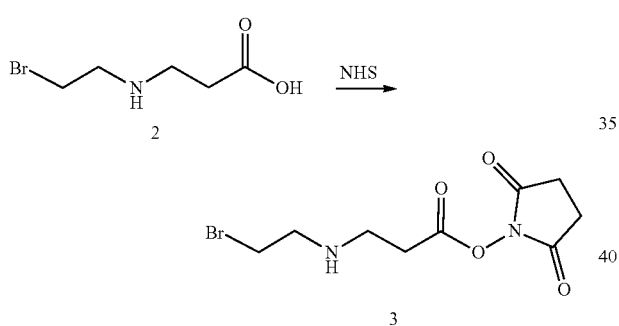

N-BABA, compound 2, is reacted with N-hydroxysuccinimide (NHS) under conventional conditions well known in the art to generate SBAP, compound 3. Specially, N-BABA is combined with at least a stoichiometric amount of NHS in a suitable inert solvent such as methanol, ethanol, isopropanol and the like. The resulting solution is stirred at about 20±5° C. until a clear solution is obtained. N-Diisopropylcarbodiimide is then added to the reaction mixture and mix with the generation of solids. The system is then cooled to 0±5° C. and resulting SBAP is provided by filtration. Further purification entails prechilling a mixture of isopropanol and heptanes and washing the filter cakes followed by drying wet cake in a vacuum oven at about 30° C. The resulting SBAP is used as is in the coupling reaction with the TT monomer.

Step 3—Conjugation

Purified TT monomer, as described above, contains 43 lysine residues/mole as quantified by a free amine assay. Reaction of TT monomer with increasing concentrations of SBAP from 0 to 170 molar equivalents led to a corresponding decrease in the free amine content over the range 15-110 molar equivalents of SBAP. A steady state conversion was achieved at SBAP charges >110 equivalents. Assuming that the loss of free amines is directly proportional to loading of SBAP linker, the linker density at saturation was estimated to be 43 moles SBAP/TT monomer.

Example 3—Oligosaccharide Synthesis

Synthesis of Building Blocks

The reaction scheme below illustrates for the synthetic steps used to prepare compounds 3, 5 and 8 that are elaborated upon below.

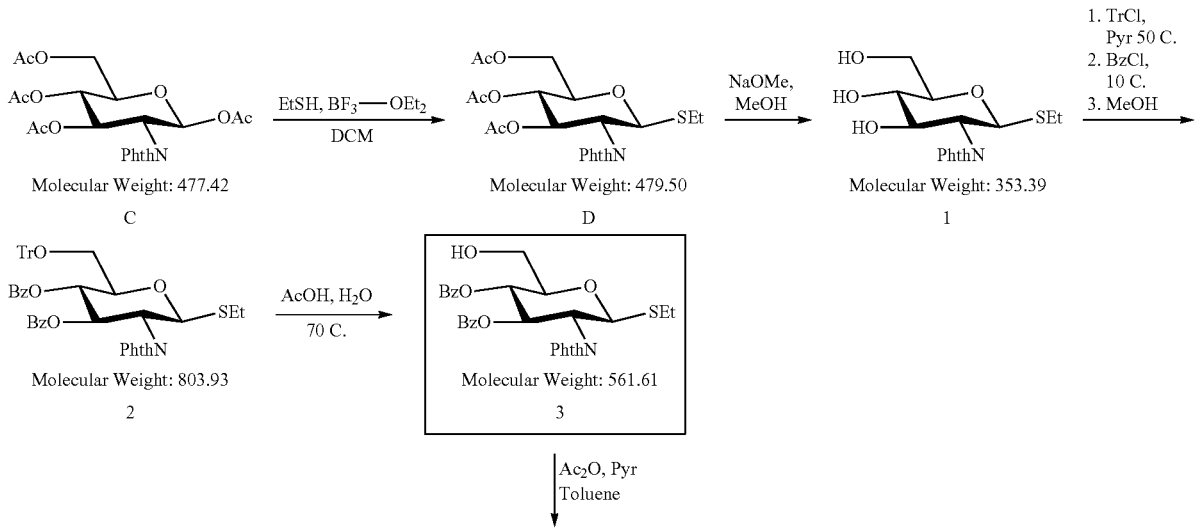

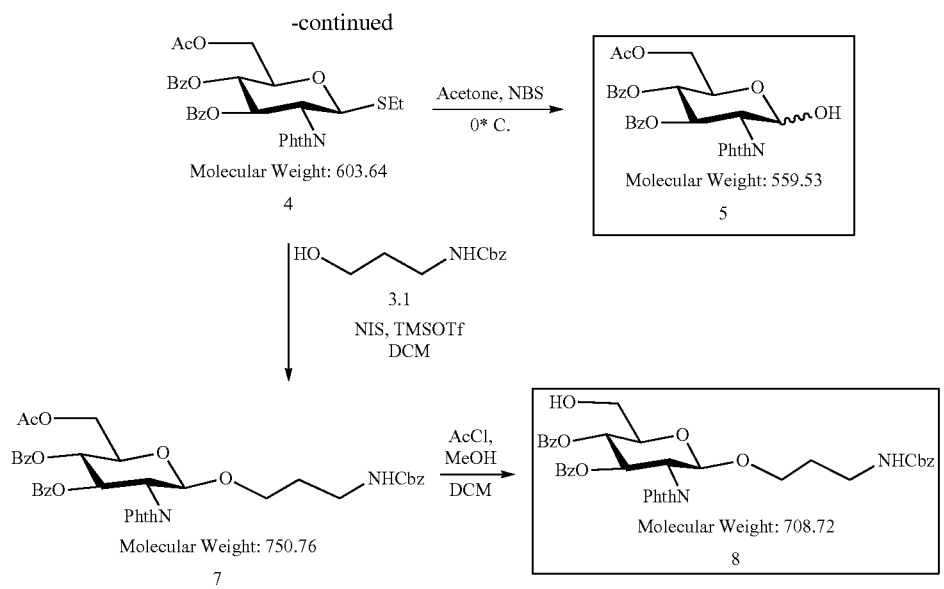

Synthesis of Compound D.

Commercially available 1,3,4,6-Tetra-O-acetyl-2-deoxy-2-N-phthalimido-β-D-glucopyranoside, compound C, (120.6 g, 252.6 mmol) and toluene (200 mL) were charged to a 1 L Büchi flask and rotated at 40° C. until dissolved (<5 minutes). The solvents were evaporated and to provide for a foam. Toluene (200 mL) was charged to the flask and rotated at 40° C. until dissolved (<5 minutes). The solvents were evaporated again until dry. A crystalline solid formed, sticking to the walls. Dichloromethane (800 mL) was charged to the flask and rotated at ambient until dissolved; the resulting dark brown solution was charged to a 5 L jacketed reactor and the flask was rinsed into the reaction with additional dichloromethane (200 mL). The heating/cooling jacket was set to 20° C. and the reactor contents were stirred mechanically. Ethanethiol (40 mL, 540 mmol) was dissolved in 50 mL dichloromethane and added to vessel and the flask rinsed with 50 ml dichloromethane into the vessel. Boron trifluoride diethyl etherate (50 mL, 390.1 mmol) was dissolved in dichloromethane (50 mL) and added to the reactor, rinsed with dichloromethane (50 mL) and added to vessel. The mixture was stirred at 20° C. for 2 h. The reaction was checked by TLC for residual C. Mobile phase was toluene: ethyl acetate (3:1, v/v), Product Rf~0.45, C Rf~0.3 with UV visualization. If significant amounts of C were present extended reaction time was required.

Stirring was set to a high speed and 4M aq. sodium acetate (1.25 L, 5100 mmol) was added. The phases were mixed well for 30 minutes. The pH of the aqueous layer was checked with a dipstick and confirmed to be ~pH=7. Stirring was turned off and the reaction mixture was left standing for 70 minutes.

The layers were separated and collected. The organic layer (bottom layer, 1.2 L) and ethanol (840 mL, 14400 mmol) were charged to the reactor. The jacket was set to 60° C. and solvent distilled under atmospheric pressure (dichloromethane bp 40° C. and ethanethiol bp 35° C., receiver flask in ice-bath). When the distillation slowed the jacket temperature was increased to 70° C. After 1300 mL of distillate were collected, a sample of the vessel content was taken and the ratio of dichloromethane to ethanol determined by $^1$H-NMR and confirmed to be under 10 mol % dichloromethane. If more dichloromethane was present further distillation would be necessary. Additional ethanol was added (400 mL) followed by seed crystals of D. The jacket was cooled to 5° C. over 30 minutes. The crystal slurry was stirred for 3 days at 5° C. The solids were collected on a sintered funnel and washed with petroleum ether (60-80° C.): 1×500 mL slurry, 1×300 mL plug. The solids were transferred to a 500 mL RBF and dried to constant weight (over ~4 h) on a rotary evaporator (bath temperature 45° C.) providing an off-white solid. Expected Yield: ~86 g (71% from C).

Synthesis of Compound 1

Anhydrous methanol (33 mL) was charged to a 50 mL round bottom flask. Sodium methoxide in methanol (30% solution, 25 µL, 0.135 mmol) was added and the resulting solution was stirred at ambient temperature for 5 minutes. Ethyl 3,4,6-tetra-O-acetyl-2-deoxy-2-N-phthalimido-β-thio-D-glucopyranoside (compound D) (3.09 g, 6.44 mmol) was added in portions (~200 mg) over 10 minutes, at a rate that allowed the solids to dissolve during addition. The reaction was stirred at ambient temperature for 2.5 h. TLC (EtOAc) showed complete consumption of compound D (Rf=0.9) and formation of one, more polar spot: Rf=0.5. A sample was taken and submitted for reaction completion IPC by HPLC (2.5 µL reaction mixture in 0.8 mL acetonitrile and 0.2 mL water), pass condition was NMT 1.00 area % Compound D. Acetic acid was added (8 µL, 0.1397 mmol). The pH was checked with a dipstick and confirmed to be ~pH 5-6. The mixture was concentrated on a rotary evaporator (50° C.) to near dryness. EtOAc (15 mL) was added and the majority evaporated. The residue was dissolved/slurried in 15 mL EtOAc and removed from the rotary evaporator. 2 mL petroleum ether was added and the mixture was stirred at ambient temperature. The crystal slurry was stirred overnight. The solids were collected on a sintered funnel, washed with petrol (2×10 mL) and dried on rotary evaporator (45° C. bath temperature) to constant weight. Expected Yield: 1.94 g (85% from Compound D).

Synthesis of Compound 2

Compound 1 (2.040 g) was dissolved in pyridine (28 mL) and the solution concentrated to approximately half the volume (~14 mL) in a rotary evaporator at 40° C. bath temperature to give a yellow solution. More pyridine was added (14 mL) and again the solution concentrated to approximately 14 mL in the same manner. The solution was placed under argon and trityl chloride (2.299 g, 1.36 eq) was added before an air-cooled condenser was attached and the solution heated to 50° C. with stirring. After 4 hours an IPC was run (HPLC; 5 µL into 800 µL MeCN, residual compound 1 NMT 3.00 area %). As soon as the IPC was met the reaction was cooled to 10-15° C. Benzoyl chloride (1.60 mL, 2.34 eq) was added dropwise over a period of 20 minutes keeping the reaction temperature below 20° C. Once addition was complete, the reaction was allowed to warm to ambient temperature and stirred for at least 3 h. At this time an IPC was run (HPLC; 5 µL into 1500 µL MeCN, residual mono-Bz derivatives of compound 1 NMT 3.00 area % total). As soon as the IPC was met the reaction was cooled to 0° C. and quenched by the slow addition of methanol (0.8 mL), ensuring the reaction temperature remains below 20° C. The quenched reaction was then warmed to ambient temperature.

The product mixture was diluted with toluene (20 mL) and stirred for 1 hour at ambient temperature before the precipitate was removed by filtering through a sintered funnel. The toluene solution was then washed with citric acid (20% w/w, 4×20 mL) followed by saturated NaHCO3 (9% w/v, 20 mL) which resulted in a minor reaction with any residual citric acid present. The toluene (upper) layer was then washed with brine (20 mL) before being evaporated in a rotary evaporator at 40° C. bath temperature to give a yellow/orange syrup (6.833 g). The syrup was submitted for IPC ($H^1$ NMR, pass condition NMT 30 wt % residual toluene). Expected Yield: ~6.833 g (147%).

Synthesis of Compound 3

Glacial acetic acid (648 mL) and ultrapure water (72 mL) were mixed together to give a 90% acetic acid solution. A portion of the acetic acid solution (710 mL) was added to crude compound 2 (111 g) along with a stirrer bar. An air cooled condenser was attached to the flask and the mixture was then heated to 70° C. Due to the viscous nature of 2, the mixture was not fully dissolved until 1 hour and 20 minutes later, at which point stirring began. After 2 hours an IPC was run (HPLC; 5 µL into 800 µL MeCN, residual compound 2 NMT 3.00 area %). As soon as the IPC met the specs, the reaction was cooled to ambient temperature. The mixture was transferred to a sintered funnel and the precipitated trityl alcohol (31.09 g) filtered off using house vacuum. The flask was rinsed with a further portion of 90% acetic acid (40 mL) and the total washings transferred to a mixing vessel. Toluene (700 mL) and water (700 mL) were added and mixed thoroughly. The aqueous (lower) layer was a cloudy white solution and was tested for pH (it was expected to be <2). The wash was repeated twice more with water (2×700 mL; pH of ~2.4 and ~3 respectively, colorless clear solutions). Saturated $NaHCO_3$ (9% w/v, 700 mL) was added to the mixing vessel resulting in a minor reaction (gas evolution). The toluene (upper) layer was then washed with brine (700 mL) before being evaporated in a rotary evaporator at 40° C. bath temperature to give a yellow/orange solid/liquid mixture (86 g). This mixture was dissolved in 400 mL toluene (300 mL+100 mL washings) and loaded on to a silica column (450 g silica) which was equilibrated with 3 column volumes (CV) of petroleum ether:toluene (1:1, v:v). The column was eluted using a stepwise gradient, fractions of 1 CV (790 mL) were collected. The gradient used was:
4 vol % ethyl acetate in petroleum ether:toluene (1:1 v:v, 4 CVs)
8 vol % ethyl acetate in petroleum ether:toluene (1:1 v:v, 12 CVs)
15 vol % ethyl acetate in petroleum ether:toluene (1:1 v:v, 4 CVs)
20 vol % ethyl acetate in petroleum ether:toluene (1:1 v:v, (4 CVs)
30 vol % ethyl acetate in petroleum ether:toluene (1:1 v:v, 1 CV)

The product eluted over 14 fractions. TLC was used to locate the product containing fractions. All fractions were submitted to IPC (HPLC, NMT 1.50 area % of the peak at 10.14 minutes and NMT 1.50 area % of the peak at 10.94 mins). Fractions not meeting IPC were set aside for processing to compound 4. The combined fractions were evaporated in a rotary evaporator at 45° C. bath temperature to give a colorless syrup. Expected Yield: ~60 g, (78%).

Synthesis of Compound 4

Crude compound 3 (39.54 g, containing ~21 g of compound 3, ~37 mmol, taken just prior to chromatography of 3) was dissolved in toluene (7.2 mL) and dry pyridine (14.2 mL, 176 mmol, ~4.8 eq.) added to give a homogenous solution. Acetic anhydride 7.2 mL (76 mmol, ~2.1 eq.) was added and the mixture stirred for 18 h at 25° C. During the reaction solids precipitate, some of this precipitate is likely to be compound 4. The reaction was sampled for IPC, if the amount of compound 3 detected was >1.00 area % then further charges of dry pyridine (1.4 mL, 17 equivs) were added and the reaction continued until residual compound 3 was ≤1.00 area % in the liquid phase.

The reaction was diluted with dichloromethane (112 mL) then water (2.8 mL) and methanol (2.8 ml) were added. The mixture was stirred for 3 h at 25° C. This stir period was shown sufficient to quench the excess acetic anhydride. The mixture was washed with citric acid monohydrate/water 20/80 w/w (112 mL). The aqueous phase was back-extracted with dichloromethane (50 mL). The dichloromethane that was used for the back-extract was set aside and used to back-extract the aqueous phases from the remaining citric acid washes. The main dichloromethane extract was returned to the vessel and the citric acid washing process repeated until the pH of the aqueous phase was ≤2 (typically two further washes). The combined citric acid washes were back-extracted. The back-extract and main dichloromethane extract were then combined. The resulting dichloromethane solution was washed with 5% w/v NaHCO3 (100 mL), the dichloromethane phase was taken and washed with water (100 mL). The dichloromethane phase was transferred to an evaporating vessel and ethyl acetate (50 mL) was added and the solution concentrated to a syrup.

Ethyl acetate (150 mL) was added and the product dissolved by heating to 55° C. with stirring. Petroleum ether 60-80 (200 mL) was added and the solution re-heated to 55° C. and held for 5 min. The solution was cooled to 45° C. and seed crystals (30 mg) added, it was then cooled to 18° C. over 3 h with stirring and held at 18° C. for at least 1 h. The crystals were collected by filtration and washed with ethyl acetate/petroleum ether (½ v/v, 60 mL). Drying in vacuo afforded compound 4 (16.04 g, 77% from 2). Expected Yield: 16.0 g (77% from Compound 2).

Synthesis of Compound 3.1

3-aminopropan-1-ol (7.01 g, 93 mmol) was dissolved in DCM (70 mL) and cooled to 0° C. Benzyl chloroformate (5.40 mL, 32 mmol) was dissolved in DCM (20 mL) and added dropwise keeping the internal reaction temp below 10° C. Once complete, the flask was stirred at room temperature for 2 h. A sample removed for NMR analysis (IPC: 20 µL+0.6 mL d6-DMSO) indicated that the benzyl chloroformate reagent had been consumed. The product mixture was then washed with citric acid (10% w/w, 2×90 mL), water (90 mL) and brine (90 mL). The DCM (lower) layer was then evaporated in a rotary evaporator at 40° C. bath temperature to give a slightly cloudy oil/liquid (6.455 g). This oil was dissolved in ethyl acetate (7 mL), warming to 40° C. if necessary to dissolve any precipitated solid, and then allowed to cool to room temperature. Petroleum ether (4 mL) was added slowly to the stirring solution along with a seed crystal, at which point the product started crystallizing slowly. Once the majority of the product had precipitated, the final portion of petroleum ether (17 mL) was then added slowly (total solvent added: ethyl acetate:petroleum ether 1:3, 21 mL). The product was then filtered under vacuum and washed with petroleum ether (5 mL) to give the product as a fine white powder (4.72 g). Expected Yield: ~4.7 g (61%).

Synthesis of Compound 5

Compound 4 (1.05 g, 1.73 mmol) was dissolved in dry acetone (12 mL, 0.06% w/w water) and water (39 µL, 2.15 mmol, 1.3 eq.) at ambient temperature. The solution was then cooled to −10° C. NBS (0.639 g, 3.59 mmol, 2.08 eq.) was added in one portion. An exotherm in the order of +7° C. was expected and the solution was then immediately re-cooled to −10° C. 15 minutes after the NBS addition, the reaction mixture was submitted for IPC (HPLC, pass condition less than 2.00 area % compound 4 remaining). If the reaction was not complete, 1.00 eq. of NBS (0.307 g, 1.73 mmol, 1.00 eq.) was added in one portion, the reaction was then held at −10° C. for another 15 minutes and a further IPC carried out. The reaction was quenched by adding aqueous $NaHCO_3$ (5% w/v, 5 mL) and cooling was stopped and the mixture allowed to warm to 10-20° C. during the following additions. After 3-5 minutes of stirring, further aqueous $NaHCO_3$ (5% w/v, 5 mL) was added and stirring continued for 5 minutes. A final aliquot of aqueous $NaHCO_3$ (5% w/v, 10 mL) was added with stirring followed by sodium thiosulfate (20% w/v, 5 mL). The mixture was stirred for 20 min. at 10-20° C. and the solids were then collected by filtration. The vessel was rinsed onto the filter pad with $NaHCO_3$ (5% w/v, 25 mL) and this rinse was filtered off. The filter cake was then rinsed successively with $NaHCO_3$ (5% w/v, 25 mL) and then water (25 mL). The (still-damp) filter cake was dissolved in DCM (20 mL) and washed with two lots of $NaHCO_3$ (5% w/v, 20 mL) and then once with water (20 mL). The dichloromethane layer was dried by rotary evaporation and then dissolved in ethyl acetate (36 mL) at 65° C. Petroleum ether 60-80 (10 mL) was then added slowly with stirring and the mixture cooled to 45° C. and stirred at 45° C. for 30 min. Additional petroleum ether 60-80 (22 mL) was added with stirring and the stirred mixture cooled to 15° C. over 2 h. The product was collected by filtration, washed with petroleum ether/ethyl acetate 2/1 v/v (20 mL) and then dried under vacuum to give compound 5 (0.805 g, 83% yield, α and β anomers combined purity by HPLC was 98%).

Synthesis of Compound 7

Compound 4 (500 mg) and intermediate 3.1 (211 mg, 1.2 eq.) were weighed into a dry flask, toluene (5 mL) was added and the solution concentrated on a rotary evaporator (45° C. bath temperature). This was repeated once more before the starting materials were concentrated from anhydrous DCM (5 mL). Once all of the solvent was removed, the residual solid was dried under vacuum for 10 minutes. Following drying, the starting materials were placed under argon, dissolved in anhydrous DCM (5.0 mL) and activated 4 Å molecular sieves (450 mg, pellet form) were added. At this point, the NIS reagent was placed under high-vacuum to dry. After 10 minutes, the dried NIS (400 mg, 2.0 equivalents) was added and the solution stirred at room temperature for 30 minutes. TMSOTf (8 µL, 5 mol %) was then added quickly, which results in the solution changing from red/orange to a deep red/brown color. The reaction temperature also rose from 22 to 27° C. As soon as the TMSOTf was added an IPC was run for information only (HPLC; 10 µL into 1 mL MeCN—$H_2O$ (8:2)). The reaction was then quenched by the addition of pyridine (20 µL, 0.245 mmol) and stirred at ambient temperature for 5 minutes. The DCM solution was filtered to remove the molecular sieves and then washed with 10% $Na_2S_2O_3$ (3×5 mL), brine (5 mL) and then concentrated on a rotary evaporator (40° C. bath temperature) to give crude compound 7 as a foamy yellow oil (616 mg). Expected Yield: ~616 mg, (99%).

Synthesis of Compound 8

Crude compound 7 (16.6 g) was dried by evaporation from toluene (2×30 mL) then from anhydrous DCM (30 mL) to produce a yellow foam/oil. The flask was then placed under an argon atmosphere before anhydrous DCM (100 mL) and dry MeOH (260 mL) was added and the mixture stirred. The flask was then cooled to 0° C. Acetyl chloride (3.30 mL, 2.0 eq.) was added dropwise while maintaining an internal temp of less than 10° C. Once addition was complete, the mixture was stirred at ambient temperature for 16 hours. At this point an IPC was run (HPLC; 20 µL into 1 mL MeCN, residual compound 7 no more than 3 area %). The flask was then cooled to 0° C. and the pH of the product solution adjusted to pH 6.5-7.5 by the addition of N-methylmorpholine (7.0 mL total required). The product mixture was diluted with DCM (50 mL) and washed with $H_2O$ (2×200 mL). The second $H_2O$ wash was cloudy and contained target material by TLC so this was back-extracted with DCM (50 mL). The combined DCM layers were then washed with brine (8 mL) before being evaporated in a rotary evaporator at 40° C. bath temperature to give an off-white foam/oil (~16.8 g). This mixture was dissolved in 140 mL toluene (100 mL+40 mL washings) and loaded onto a silica column (85 g silica) which was equilibrated with 3 column volumes (CV) of 30 vol % ethyl acetate in petroleum ether. The column was eluted using a stepwise gradient, fractions of 1 CV (140 mL) were collected. The gradient used was:

30 vol % ethyl acetate in petroleum ether (3 CVs)

35 vol % ethyl acetate in petroleum ether (4 CVs)

40 vol % ethyl acetate in petroleum ether (9 CVs)

50 vol % ethyl acetate in petroleum ether (4 CVs)

60 vol % ethyl acetate in petroleum ether (3 CVs)

The product eluted over 12 fractions. All fractions were submitted to IPC (HPLC, NMT 1.50 area % of any impurity peak at 230 nm). The combined fractions were evaporated in a rotary evaporator at 40° C. bath temperature to give an off-white foam which solidified to afford 8 as a crunchy solid (10.45 g). Expected Yield: 10.45 g (66%).

Example 4—Synthesis of Disulfide (Compound 17)
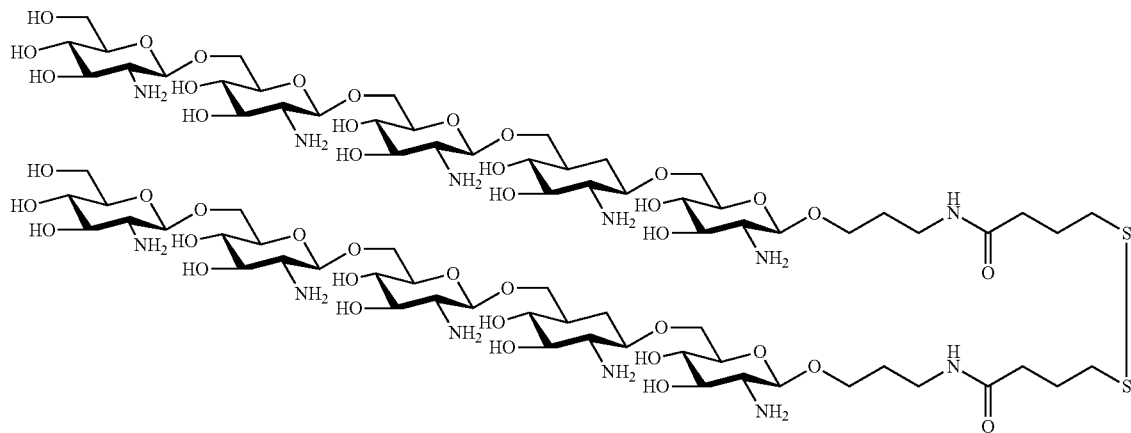
Compound 17
The overall synthetic procedure for the synthesis of compound 17 is described in the synthetic scheme below.

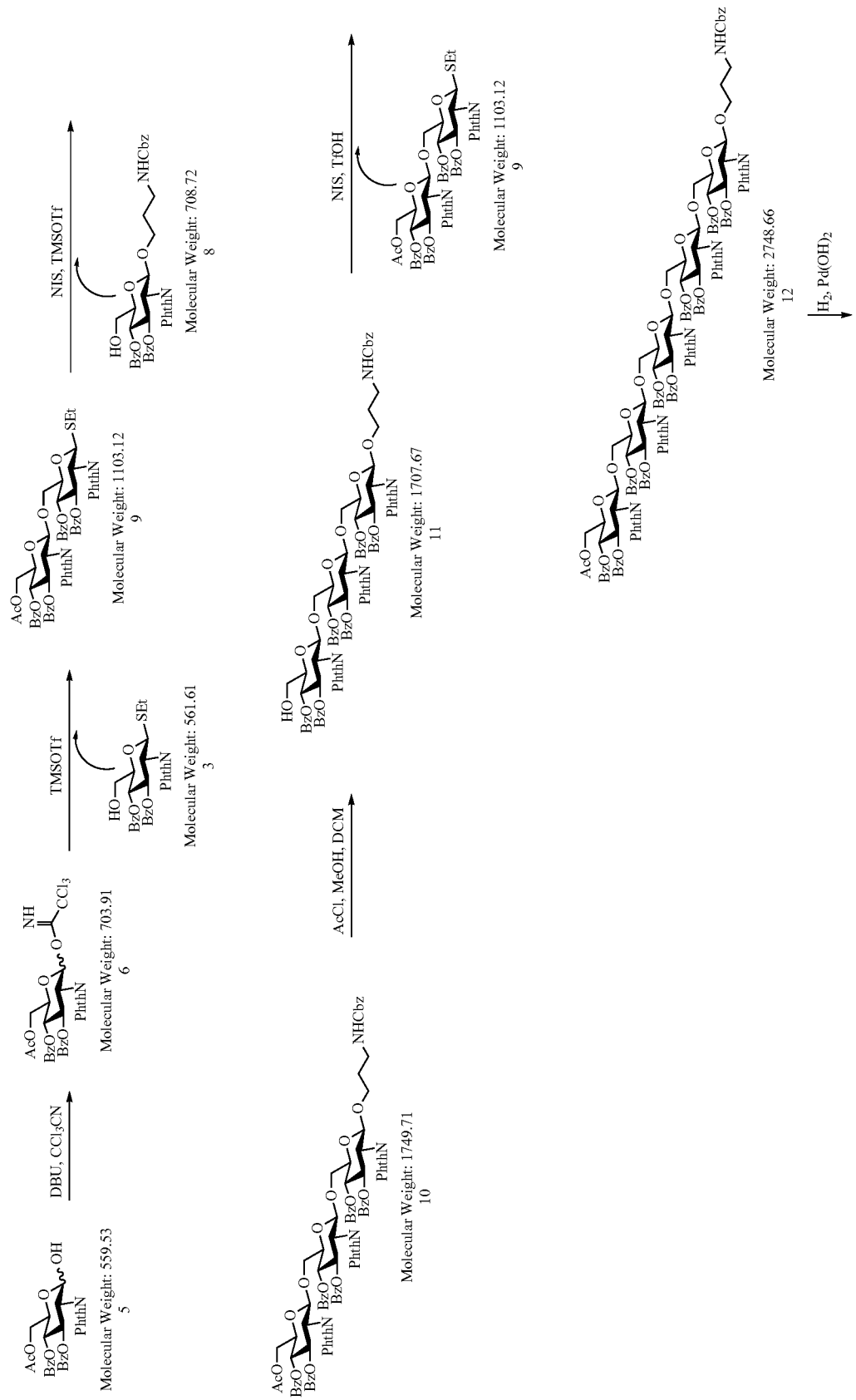

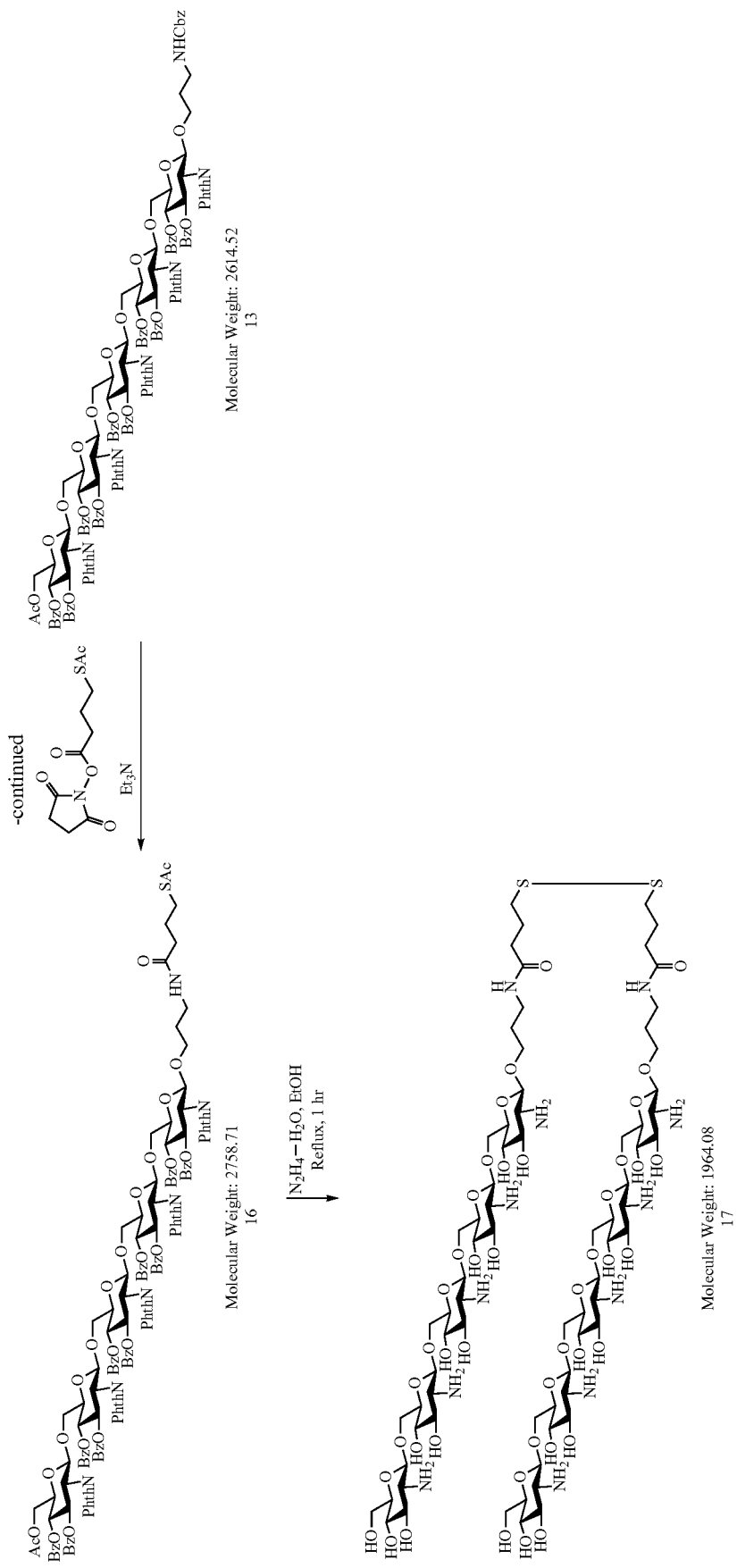

Synthesis of Compound 9

Compound 5 (1620 g, 1.18 eq.) and toluene (18 kg) were charged to a 50 L Büchi bowl in that order. The bowl was warmed in a water bath with a setting of 50±10° C. for 30 min. Evaporation was run under vacuum using a water bath temperature of 50±10° C. until no more solvent distilled. The water bath was cooled to 20±10° C. Trichloroacetonitrile (7.1 kg, 21 equiv.) and dry DCM (6.5 kg) were charged to the bowl under nitrogen atmosphere. A suspension of sodium hydride (5.6 g, 0.060 equiv.) in dry DCM (250 g) was charged to the bowl under nitrogen atmosphere. The bowl contents were mixed by rotation for 1-2 h with a water bath temperature of 20±10° C. Compound 5 dissolved during the reaction. The bowl contents were sampled and submitted for reaction completion IPC ($H^1$ NMR, integrating triplet peak at 6.42 ppm (product) relative to triplet at 6.35 ppm (starting material); pass condition ≤5% residual starting material). Compound 3 (1360 g, 2.35 mol), dry DCM (12.3 kg) and powdered molecular sieves 4 Å (136 g) were charged to the 50 L reactor in that order. The reactor contents were mixed for 24 h. The reactor contents were sampled through a syringe filter and analyzed by Karl Fisher (AM-GEN-011, pass condition ≤0.03% w/w). After reaching the moisture threshold (~24 h), the reactor contents were adjusted to 0±5° C. The contents of the Büchi bowl were transferred to the reactor header as volume allowed. A solution of trimethylsilyl trifluoromethanesulfonate (100 g, 0.18 eq.) in dry DCM (1250 g) was charged to the reactor under a nitrogen atmosphere. The header contents were drained to the reactor maintaining the reactor contents at 0±10° C. throughout the addition. Addition took 15-20 min. Dry DCM (1250 g) was charged to the Büchi bowl and then transferred to the reactor header. The header contents were drained to the reactor maintaining the reactor contents at 0±10° C. throughout the addition. The reactor contents were stirred at 0±5° C. for 60 min. The reactor contents were sampled for reaction completion using IPC (HPLC, pass criteria ≤5% starting material). The reaction was quenched by charging N-methylmorpholine (85 g, 0.36 eq.) to the reactor. The reactor contents were sampled for quench completion using IPC (wetted pH paper, pass criteria ≥pH 7). Silica gel (4.9 kg) was charged to the Büchi bowl. The reactor contents were transferred to the Büchi bowl. Evaporation was run under vacuum using a water bath temperature of 40±10° C. until no more solvent distilled. Silica gel (1.4 kg) was charged to the Büchi bowl followed by dichloromethane (7.0 kg) used to rinse the reactor. The bowl contents were rotated to ensure solids were not adhered to the bowl surface. Evaporation was run under vacuum using a water bath temperature of 40±10° C. until no more solvent distilled. The bowl contents were divided into three portions for silica gel chromatography. A 150 L KP-SIL cartridge was installed in the Biotage system. Ethyl acetate (7.8 kg) and petroleum ether (22 kg) were charged to the 50 L reactor along with ⅓ of the reaction mixture adsorbed onto silica gel, mixed thoroughly and then transferred to a Biotage solvent reservoir. The solvent reservoir contents were eluted through the column so as to condition the column. The eluent was collected in 20 L jerry cans and discarded. The column was run in three batches and each was eluted with ethyl acetate/petroleum ether as described below:

a. Ethyl acetate (1.6 kg) and Petroleum ether (4.4 kg) were charged to a Biotage solvent reservoir, mixed thoroughly and then eluted through the column. Column run-off was collected in 20 L jerry cans.
b. Ethyl acetate (25 kg) and Petroleum ether (26 kg) were charged to the 50 L reactor, mixed thoroughly, transferred to two Biotage solvent reservoirs and then eluted through the column. Column run-off was collected in 20 L jerry cans.
c. Ethyl acetate (31 kg) and Petroleum ether (22 kg) were charged to the 50 L reactor, mixed thoroughly, transferred to two Biotage solvent reservoirs and then eluted through the column. Column run-off was collected in 5 L glass lab bottles.
d. Ethyl acetate (16 kg) was charged to a Biotage solvent reservoir and then eluted through the column. Column run-off was collected in 20 L jerry cans.
e. The column was repeated as above with the remaining two portions of dry load silica prepared.

The column fractions were sampled for product purity (TLC [10% acetone in toluene, Rf 0.5]) to identify fractions with product. The accepted column fractions were combined and in a 100 L Büchi bowl. Toluene was used to rinse any crystalline material from accepted fraction vessels into the bowl. Evaporation was run under vacuum using a water bath temperature of 40±10° C. until no more solvent distilled. Toluene (1.7 kg) was charged to the bowl and to contents rotated until the solids dissolved. t-Butyl methyl ether (4.4 kg) was charged to the bowl over 20-40 min. The bowl contents were rotated for 12-24 h at a temperature of 20±5° C. The bowl contents were transferred to a 6 L Nutsche filter and the solvent removed by vacuum filtration. t-Butyl methyl ether (620 g) was charged to the bowl, transferred to the Nutsche filter and passed through the filter cake. The filter cake was air dried in the filter then transferred to a vacuum oven and dried at a setting of 30° C. under vacuum to remove residual solvent. The solid was sampled for analytical and retention. The solid was transferred to screw-top Nalgene containers and stored at ≤−15° C. Expected Yield: 1.68-1.94 kg compound 9 (65-75%).

Synthesis of Compound 10

Reagents were prepared as follows: N-Iodosuccinimide (241 g, 2.20 eq.) was dried in a vacuum oven with a setting of 30° C. under vacuum for 24 h. A solution of sodium chloride (300 g) in water (3000 g) was prepared in a 5 L lab bottle. A solution of sodium thiosulfate (1100 g) in water (6000 g) was prepared in a 50 L reactor and distributed into two portions.

Compound 8 (355 g, 0.486 mol) and Compound 9 (634 g, 1.10 eq.) were charged to a 20 L Büchi bowl followed by toluene (1500 g) and heated at 40±5° C. until dissolved. Evaporation was run under vacuum using a water bath temperature of 35±10° C. until no more solvent distilled. Toluene (1500 g) was charged to the Büchi bowl. Evaporation was run under vacuum using a water bath temperature of 35±10° C. until no more solvent distilled. Dry dichloromethane (4000 g) was charged to the Büchi bowl. The bowl was rotated until the solids dissolved and the solution was transferred to a 5 L reactor with a jacket temperature of 20° C.±5° C. Dry dichloromethane (710 g) was charged to the Büchi bowl. The bowl was rotated to rinse the bowl surface and the solution was transferred to the 5 L reactor. The reactor contents were sampled for reagent ratio IPC ($H^1$ NMR). Dried N-Iodosuccinimide was charged to the reactor under a nitrogen atmosphere and the reactor was stirred for 5-15 min. The reactor contents were adjusted to 20° C.±3° C. Trimethylsilyl trifluoromethanesulfonate (5.94 g, 0.055 eq.) in dry DCM (60 g) was charged to the reactor over 5-15 min. maintaining the contents temperature at 20° C.±3° C. The reaction mixture was stirred at 20° C.±3° C. for 20±3 min. The reactor contents were sampled for reaction completion (HPLC). N-Methylmorpholine (98 g, 2 equiv.) was charged to the reactor and mixed thoroughly. One of the portions of the sodium thiosulfate solution prepared above was charged to the 50 L reactor. The 5 L reactor contents were transferred to the 50 L reactor containing the sodium thiosulfate solution and mixed thoroughly. The bottom layer was discharged to a HDPE jerry can.

DCM (570 g) was charged to the 5 L reactor with the top layer from the 50 L reactor and mixed thoroughly. The bottom layer was combined with the previous bottom layer in the HDPE jerry can. The top layer was transferred to a separate HDPE jerry can and retained until yield was confirmed. The combined organic phase (bottom layers) were charged to the 50 L reactor followed by another portion of sodium thiosulfate and mixed thoroughly. The bottom layer was discharged to a HDPE jerry can. The top layer was retained in a HDPE jerry can until yield was confirmed. The sodium chloride solution was charged to the 50 L reactor along with the organic phase (bottom layers) and mixed thoroughly. Silica gel (1300 g) was charged to a Büchi bowl and fitted with a rotary evaporator. The bottom layer in the reactor was charged to the Büchi bowl. The bowl contents were rotated to prevent adsorption onto the bowl and evaporated under vacuum using a water bath temperature of 40±5° C. until no more solids distilled. The bowl contents were divided into two equal portions. Silica gel (200 g) was charged to the Büchi bowl followed by dichloromethane (700 g). The bowl contents were rotated to ensure solids did not adhere to the bowl surface. The bowl was evaporated under vacuum at a water bath temperature of 40° C.±10° C. until no more solvent distilled. The bowl contents were divided into two portions and a portion was added to each of the previous silica gel samples.

Each portion was purified independently on silica gel using the following procedure (samples were stored at ≤15° C. while awaiting purification): A 150 L KP-SIL cartridge was installed in the Biotage system. Ethyl acetate (15.5 kg) and petroleum ether (16.5 kg) were charged to the 50 L reactor, mixed thoroughly and then transferred to two Biotage solvent reservoirs. The solvent reservoirs contents were eluted through the column so as to condition the column. The eluent was collected in 20 L jerry cans and discarded. A portion of the dry load silica from above was charged to the Biotage Sample-Injection Module (SIM) and then eluted with the ethyl acetate/petroleum ether as follows:
a. Ethyl acetate (6.2 kg) and Petroleum ether (6.6 kg) were charged to a 50 L reactor, mixed thoroughly and then transferred to a Biotage solvent reservoir. Column run-off was collected in 20 L jerry cans.
b. Ethyl acetate (19.5 kg) and Petroleum ether (19.2 kg) were charged to the 50 L reactor, mixed thoroughly, transferred to two Biotage solvent reservoirs and then eluted through the column. Column run-off was collected in 20 L jerry cans.
c. Ethyl acetate (13.6 kg) and Petroleum ether (12.3 kg) were charged to the 50 L reactor, mixed thoroughly, transferred to two Biotage solvent reservoirs and then eluted through the column. Column run-off was collected in 20 L jerry cans.
d. Ethyl acetate (14.2 kg) and Petroleum ether (11.9 kg) were charged to the 50 L reactor, mixed thoroughly, transferred to two Biotage solvent reservoirs and then eluted through the column. Column run-off was collected in 20 L jerry cans.
e. Ethyl acetate (29.7 kg) and Petroleum ether (22.9 kg) was charged to a Biotage solvent reservoir and then eluted through the column. Column run-off was collected in 20 L jerry cans up to fraction 11 and then 5 L HDPE jerry cans.
f. Ethyl acetate (15.5 kg) and Petroleum ether (11.0 kg) was charged to a Biotage solvent reservoir and then eluted through the column. Column run-off was collected in 5 L HDPE jerry cans.
g. Ethyl acetate (29.7 kg) and Petroleum ether (13.2 kg) was charged to a Biotage solvent reservoir and then eluted through the column. Column run-off was collected in 5 L HDPE jerry cans.
h. Ethyl acetate (15.5 kg) was charged to a Biotage solvent reservoir and then eluted through the column. Column run-off was collected in 5 L HDPE jerry cans.

Column fractions were sampled for product purity (TLC to identify fractions with product). Fractions that were 75-95% area compound 10 from the first two columns were combined in a Büchi bowl charged with silica gel (400 g) and evaporation was run under vacuum using a water bath temperature of 40±10° C. until no more solvent distilled. The contents of the bowl were purified as follows: A 150 L KP-SIL cartridge was installed in the Biotage system. Ethyl acetate (15.5 kg) and petroleum ether (16.5 kg) were charged to the 50 L reactor, mixed thoroughly and then transferred to two Biotage solvent reservoirs. The solvent reservoirs contents were eluted through the column so as to condition the column. The eluent was collected in 20 L jerry cans and discarded. The bowl contents were charged to the Biotage Sample-Injection Module (SIM) and then eluted with the ethyl acetate/petroleum ether as follows:
a. Ethyl acetate (6.2 kg) and Petroleum ether (6.6 kg) were charged to a 50 L reactor, mixed thoroughly and then transferred to a Biotage solvent reservoir. Column run-off was collected in 20 L jerry cans.
b. Ethyl acetate (19.5 kg) and Petroleum ether (19.2 kg) were charged to the 50 L reactor, mixed thoroughly, transferred to two Biotage solvent reservoirs and then eluted through the column. Column run-off was collected in 20 L jerry cans.
c. Ethyl acetate (13.6 kg) and Petroleum ether (12.3 kg) were charged to the 50 L reactor, mixed thoroughly, transferred to two Biotage solvent reservoirs and then eluted through the column. Column run-off was collected in 20 L jerry cans.
d. Ethyl acetate (14.2 kg) and Petroleum ether (11.9 kg) were charged to the 50 L reactor, mixed thoroughly, transferred to two Biotage solvent reservoirs and then eluted through the column. Column run-off was collected in 20 L jerry cans.
e. Ethyl acetate (29.7 kg) and Petroleum ether (22.9 kg) was charged to a Biotage solvent reservoir and then eluted through the column. Column run-off was collected in 20 L jerry cans up to fraction 11 and then 5 L HDPE jerry cans.
f. Ethyl acetate (15.5 kg) and Petroleum ether (11.0 kg) was charged to a Biotage solvent reservoir and then eluted through the column. Column run-off was collected in 5 L HDPE jerry cans.
g. Ethyl acetate (29.7 kg) and Petroleum ether (13.2 kg) was charged to a Biotage solvent reservoir and then eluted through the column. Column run-off was collected in 5 L HDPE jerry cans.
h. Ethyl acetate (15.5 kg) was charged to a Biotage solvent reservoir and then eluted through the column. Column run-off was collected in 5 L HDPE jerry cans.

The accepted column fractions from all three columns were combined in a Büchi bowl and evaporation was run under vacuum using a water bath with temperature of 40° C.±10° C. until no more solvent distilled. The contents of the bowl was sampled for analytical and retention. The bowl was sealed and transferred to storage at ≤−15° C. Expected Yield: 440-540 kg (52-64% yield).

Synthesis of Compound 11

Dichloromethane was charged to a Büchi bowl containing compound 10 (635 g, 0.345 mol) (PN0699) and heated at 30±10° C. until dissolved. Methanol (3.2 kg) was charged to the bowl. The content of the bowl were adjusted to 0±3° C. Acetyl chloride (54.1 g, 2 equiv.) in dichloromethane (660 g) was charged to the bowl maintaining the contents temperature at 0±10° C. The bowl contents were adjusted to 20±3° C. and the mixture was stirred for 40-48 h. The bowl contents were sampled for reaction completion IPC (HPLC, pass). The bowl contents were adjusted to 0±3° C. N-methylmorpholine (139 g, 4 equiv.) was charged to the bowl and mixed thoroughly. The bowl contents were sampled for quench completion IPC (pH paper, pass ≤pH7). The bowl contents were concentrated under vacuum with water bath at 35±10° C. Ethyl acetate (4.8 kg) and water (5.5 kg) were charged to the Büchi bowl and rotated to dissolve the bowl contents. The bowl contents were transferred to a 50 L reactor and mixed thoroughly. The bottom layer was drained to a HDPE jerry can. The top layer was transferred to a Büchi bowl fitted with a rotary evaporator and the contents were concentrated under vacuum with a water bath at 35±10° C. The bottom layer from the HDPE jerry can was charged to a 50 L reactor with ethyl acetate (1.5 kg) and mixed thoroughly. The bottom layer was drained to a HDPE jerry can and held until yield was confirmed. The top layer was transferred to the Büchi bowl fitted with a rotary evaporator and the contents were concentrated under vacuum with a water bath at 35±10° C. The contents of the bowl were sampled for analytical and retention. The bowl was sealed and transferred to storage at ≤−15° C. Expected Yield: 518-633 kg (90-110% yield).

Synthesis of Compound 12

Reagents were prepared as follows: Two portions of N-Iodosuccinimide (143 g, 3.90 eq.) were dried in a vacuum oven with a setting of 30° C. under vacuum for 24 h. A solution of sodium chloride (450 g) in water (1850 g) was prepared in a 5 L lab bottle and distributed to 2 approximately equal portions. A solution of sodium thiosulfate (230 g) in water (2080 g) was prepared in a 5 L lab bottle and distributed to 4 approximately equal portions. Compound 9 (504 g, 1.30 eq.) was charged to a 50 L Büchi bowl containing compound 11 (607 g, 0.327 mol) followed by toluene (1500 g) and heated at 40±5° C. until dissolved. Evaporation was run under vacuum using a water bath temperature of 35±10° C. until no more solvent distilled. Toluene (1500 g) was charged to the Büchi bowl. Evaporation was run under vacuum using a water bath temperature of 35±10° C. until no more solvent distilled. Dry DCM (2400 g) was charged to the Büchi bowl. The bowl was rotated until the solids dissolved and half the solution transferred to the 5 L reactor with a jacket temperature of 20° C.±5° C. The second half of the solution was transferred to a 5 L lab bottle. Dry DCM (710 g) was charged to the Büchi bowl. The bowl was rotated to rinse the bowl surface and half the solution was transferred to the 5 L reactor. The other half was charged to the 5 L lab bottle above and stored under nitrogen for use in the second batch. A portion of dried N-Iodosuccinimide was charged to the reactor under a nitrogen atmosphere. The reactor contents were adjusted to −40° C.±3° C. Trimethylsilyl trifluoromethanesulfonate (9.09 g, 0.25 effective equiv.) in dry dichloromethane (90 g) was charged to the reactor over 15 min. maintaining the contents temperature at −40° C.±5° C. The reaction mixture was stirred at −40° C.±3° C. for 30±5 min. then adjusted to −30° C.±3° C. over and stirred for 150 min. The reactor contents were sampled for reaction completion. N-Methylmorpholine (33.1 g, 2 effective eq.) was charged to the reactor and mixed thoroughly. One of the portions of the sodium thiosulfate solution prepared above was charged to the 5 L reactor and mixed thoroughly. The bottom layer was discharged to a 5 L lab bottle. DCM (400 g) was charged to the 5 L reactor and mixed thoroughly. The bottom layer was combined with the previous bottom layer in a 5 L lab bottle. The combined organic phases were charged to the 5 L reactor followed by another portion of sodium thiosulfate and mixed thoroughly. The bottom layer was discharged to a 5 L lab bottle. A portion of sodium chloride solution from above was charged to the reactor followed by the content of the previous lab bottle. The bottom layer in the reactor was charged to the Büchi and evaporated under vacuum using a water bath temperature of 40±10° C. until no more solvent distilled. The reactor was cleaned and dried.

The second portion of compound 9 and compound 11 were charged to the reactor and treated identically to first batch. Following organic extraction of the second batch, the reaction mixtures were combined in the reactor. A portion of sodium chloride solution was charged to the reactor and mixed thoroughly. Silica gel (1700 g) was charged to a Büchi bowl and fitted to a rotavapor. The bottom layer in the reactor was charged to the Büchi and evaporated under vacuum using a water bath temperature of 40±10° C. until no more solvent distilled. The bowl contents were divided into two portions purified independently on silica gel. A 150 L KP-SIL cartridge was installed in the Biotage system (commercially available from Biotage, a division of Dyax Corporation, Charlottesville, Va., USA). Ethyl acetate (7.7 kg) and petroleum ether (22.0 kg) were charged to the 50 L reactor, mixed thoroughly and then transferred to two Biotage solvent reservoirs. The solvent reservoirs contents were eluted through the column so as to condition the column. The eluent was collected in 20 L jerry cans and discarded. A portion of the dry load silica from above was charged to the Biotage Sample-Injection Module (SIM) and then eluted with the ethyl acetate/petroleum ether as follows:

a. Ethyl acetate (1.5 kg) and Petroleum ether (4.4 kg) were charged to a HDPE jerry can, mixed thoroughly and then transferred to a Biotage solvent reservoir. Column run-off was collected in 20 L jerry cans.

b. Ethyl acetate (18.6 kg) and Petroleum ether (8.8 kg) were charged to the 50 L reactor, mixed thoroughly, transferred to two Biotage solvent reservoirs and then eluted through the column. Column run-off was collected in 20 L jerry cans.

c. Ethyl acetate (19.2 kg) and Petroleum ether (8.4 kg) were charged to the 50 L reactor, mixed thoroughly, transferred to two Biotage solvent reservoirs and then eluted through the column. Column run-off was collected in 20 L jerry cans.

d. Ethyl acetate (29.7 kg) and Petroleum ether (11.9 kg) were charged to the 50 L reactor, mixed thoroughly, transferred to two Biotage solvent reservoirs and then eluted through the column. Column run-off was collected in 20 L jerry cans.

e. Ethyl acetate (15.5 kg) was charged to a Biotage solvent reservoir and then eluted through the column. Column run-off was collected in 5 L glass lab bottles.

Column fractions were sampled for product purity (TLC to identify fractions with product). Fractions that were 75-95% area compound 12 from the first two columns were combined in a Büchi bowl charged with silica gel (400 g) and evaporation was run under vacuum using a water bath temperature of 40±10° C. until no more solvent distilled. Ethyl acetate (7.7 kg) and petroleum ether (22.0 kg) were charged to the 50 L reactor, mixed thoroughly and then transferred to two Biotage solvent reservoirs. The solvent reservoirs contents were eluted through the column so as to condition the column. The eluent was collected in 20 L jerry cans and discarded. The dry load silica containing the impure product was charged to the Biotage Sample-Injection Module (SIM) and then eluted as detailed below:

a. Ethyl acetate (1.5 kg) and Petroleum ether (4.4 kg) were charged to the 50 L reactor, mixed thoroughly and then transferred to a Biotage solvent reservoir. Column run-off was collected in 20 L jerry cans.
b. Ethyl acetate (19.2 kg) and Petroleum ether (8.4 kg) were charged to the 50 L reactor, mixed thoroughly, transferred to two Biotage solvent reservoirs and then eluted through the column. Column run-off was collected in 20 L jerry cans.
c. Ethyl acetate (18.6 kg) and Petroleum ether (8.8 kg) were charged to the 50 L reactor, mixed thoroughly, transferred to two Biotage solvent reservoirs and then eluted through the column. Column run-off was collected in 20 L jerry cans.
d. Ethyl acetate (29.7 kg) and Petroleum ether (11.9 kg) were charged to the 50 L reactor, mixed thoroughly, transferred to two Biotage solvent reservoirs and then eluted through the column. Column run-off was collected in 20 L jerry cans.
e. Ethyl acetate (15.5 kg) was charged to a Biotage solvent reservoir and then eluted through the column. Column run-off was collected in 5 L glass lab bottles.

Column fractions were sampled for product purity (TLC to identify fractions with product, HPLC pass criteria ≥95% compound 12 and no single impurity >2.5%). The accepted column fraction from all three columns were combined in a Büchi bowl and evaporation was run under vacuum using a water bath temperature of 40±10° C. until no more solvent distilled. The contents of the bowl was sampled for analytical and retention. Bowl was sealed and transferred to storage at ≤−15° C. Expected Yield: 494-584 kg (52-64% yield).

Synthesis of Compound 13

Glacial acetic acid (7.5 kg) and ethyl acetate (6.5 kg) were combined in a suitable container and labeled as "GAA/EA solution". Sodium bicarbonate (0.5 kg) was dissolved in RO water (10 kg) and labelled as "5% w/w sodium bicarbonate solution." Palladium on activated carbon (100 g, specifically Johnson Matthey, Aliso Viejo, Calif., USA, Product No. A402028-10) and GAA/EA solution (335 g) was charged into a reaction vessel in that order. Compound 12 (270 g) was dissolved in GAA/EA solution (1840 g) and transferred to a 50 L reaction vessel. The solution was purged of oxygen by pressurization with nitrogen to 10 bar and then released. This was repeated twice more. The reactor contents were pressurized under hydrogen to 10 bar and then released. The reaction mixture was hydrogenated at 20 bar $H_2$ for 1.5 days. The pressure was then released and the solution purged of hydrogen by pressurization with nitrogen to 10 bar and then release. This was repeated once. Reaction mixture was filtered through a pad of Celite (300 g). The celite cake was washed with GAA/EA solution (2×5.5 kg). Filtrates were combined and evaporated under vacuum (bath temperature 40±5° C.). The residue was co-evaporated with ethyl acetate (2.3 kg) in two portions. The expected weight of the crude product was ~316 g. A Biotage system was equipped with 150 M KP-SIL cartridge with a 5 L Sample Injection Module (SIM). Ethyl acetate (10.6 kg) and glacial acetic acid (1.4 kg) were charged to the 50 L reactor, mixed thoroughly and then transferred to a Biotage solvent reservoir. The contents of the solvent reservoir were eluted through the column so as to condition the column. The eluent was discarded. The crude product was dissolved in ethyl acetate (422 g) and glacial acetic acid (55 g). The resulting solutions were charged to the SIM and passed onto the column. The reaction mixture was chromatographed as follows:

a. Ethyl acetate (13.8 kg) and glacial acetic acid (1.8 kg) were charged to the 50 L reactor, mixed thoroughly and then transferred to a Biotage solvent reservoir.
b. The contents of the solvent reservoir were eluted through the SIM onto the column and the eluent was collected in a 20 L jerry can.
c. Ethyl acetate (10.3 kg), glacial acetic acid (1.3 kg) and methanol (206 g) were charged to the 50 L reactor, mixed thoroughly and then transferred to a Biotage solvent reservoir.
d. The contents of the solvent reservoir were eluted through the column and the eluent was collected in a 5 L jerry cans.
e. Ethyl acetate (6.6 kg), glacial acetic acid (0.9 kg) and methanol (340 g) were charged to the 50 L reactor, mixed thoroughly and then transferred to a Biotage solvent reservoir.
f. The contents of the solvent reservoir were eluted through the column and the eluent was collected in ~2.5 L fractions in 5 L jerry cans.
g. Ethyl acetate (31.4 kg), glacial acetic acid (4.1 kg) and methanol (3.4 kg) were charged to the 50 L reactor, mixed thoroughly and then transferred to a Biotage solvent reservoir.
h. The contents of the solvent reservoir were eluted through the column and the eluent was collected in 5 L jerry cans.

Fractions containing compound 13 were combined and evaporated under vacuum (bath temperature 40±5° C.). Residue was dissolved in ethyl acetate (3.1 kg) and washed with 5% w/w sodium bicarbonate solution (9.3 kg), ensuring the pH of the aqueous medium was ≥8. The ethyl acetate phase was evaporated under vacuum (bath temperature 40±5° C.). The contents of the bowl was sampled for analytical and retention. Expected Yield: 182-207 g (71-81%).

Synthesis of Compound 16

Dry dichloromethane (2.5 kg) was charged to a Büchi bowl containing compound 13 (211 g, 76.5 mmol, 1.00 eq.) and rotated without heating until dissolved. A solution of (2,5-dioxopyrrolidin-1-yl) 4-acetylsulfanylbutanoate (25.8 g, 99.4 mmol, 1.30 equiv) in dry dichloromethane (200 g) was added to the Büchi bowl. The bowl was rotated for 1 hr at ambient temperature followed by concentration under vacuum with a water bath temperature of 40±5° C. Toluene (0.8 kg) was added to the bowl and removed under vacuum with a water bath temperature of 40±5° C. twice. Toluene (0.8 kg) was added to the residue to dissolve. Silica gel (557 g) was loaded into the reaction vessel and solvents were removed under vacuum with a water bath temperature of 40±5° C. A Biotage system was equipped with a 150 M KP-SIL cartridge with a 5 L Sample Injection Module (SIM). Toluene (10.1 kg) and acetone (1.0 kg) were charged to the 50 L reactor, mixed thoroughly and then transferred to a Biotage solvent reservoir (Solvent A). The reaction mixture was purified as follows:

a. Solvent A was eluted through the column so as to condition the column. The eluent was discarded.
b. Dry loaded silica gel was transferred to the SIM.

c. Toluene (9.6 kg) and acetone (1.5 kg) were charged to the 50 L reactor, mixed thoroughly and then transferred to a Biotage solvent reservoir (Solvent B).
d. Solvent B was eluted through the column and the eluent was collected in 5 L jerry cans.
e. Toluene (53.6 kg) and acetone (12.2 kg) were charged to the 50 L reactor, mixed thoroughly and then transferred to Biotage solvent reservoirs (Solvent C).
f. Solvent C was eluted through the column and the eluent is collected in 5 L jerry cans.
g. Toluene (8.4 kg) and acetone (2.6 kg) were charged to the 50 L reactor, mixed thoroughly and then transferred to a Biotage solvent reservoir (Solvent D).
h. Solvent D was eluted through the column and the eluent was collected in a 5 L jerry cans.
i. Toluene (23.4 kg) and acetone (9.2 kg) were charged to the 50 L reactor, mixed thoroughly and then transferred to a Biotage solvent reservoir (Solvent E).
j. Solvent E was eluted through the column and the eluent was collected in a 5 L jerry cans.

Fractions containing compound 16 (pass criteria ≥90% compound 16 and no single impurity >2.5%) were combined and evaporated under vacuum (bath temperature 40±5° C.). The residue was dissolved in tetrahydrofuran (4.4 kg) and concentrated under vacuum with a water bath temperature of 40±5° C. The contents of the bowl were sampled for analytical and retention. Expected Yield: 169-192 g (76-86%).

Synthesis of Compound 17

The reactor was marked at the 2.5 L, 3.5 L and 3.9 L levels before starting and fit with a vacuum controller. Dichloromethane was charged to a Büchi Bowl containing 140 g of compound 16 and transferred to the Reactor Ready vessel. Two rinses of DCM (333 g) were used to transfer the contents of the Büchi bowl into the Reactor Ready vessel. Ethanol (2.50 kg) was added to the reactor ready. The reaction mixture was concentrated to the 2.5 L mark (target vacuum 250 mbar). Ethanol (1.58 kg) was added to the reactor ready and concentrated to the 3.5 L mark. The reaction was diluted to the 3.9 L mark with ethanol. Reactor contents were placed under inert gas by applying a partial vacuum and releasing with nitrogen. A slow flow of nitrogen was maintained during the reaction. Hydrazine monohydrate (1.13 kg, 1.11 L) was charged to the 5 L Reactor Ready vessel under a nitrogen atmosphere. The temperature ramp was set to: initial temp 20° C., final temp 60° C., with a linear temperature ramp over 50 min (0.8 deg/min) and active control on the contents of the reactor. The vessel temperature was held at 60° C. for 45 min. The cooling ramp temperature was set to: −2 deg/min, with the final temp 20° C. The contents were discharged to suitable HDPE jugs and weights determined. Equal amounts were transferred to 8 polypropylene centrifuge containers with FEP encapsulated seals. Each centrifuge container was charged with ethanol (750 g) and agitated for 30 min at ambient. The containers were centrifuged (5300 RCF, 15° C., 30 min). Residual hydrazine on the outside of the containers was removed by rinsing the outside of the bottles with acetone then water before taking out of fume hood. The supernatant in the centrifuge containers was decanted and the residual pellet was dissolved in Low Endotoxin water (LE water) (1960 g) and transferred to a 5 L Reactor Ready vessel. The contents were agitated at medium speed while bubbling air through the solution using a dispersion tube approximately 15-20 min for every 1.5 hrs. The reaction was then stirred overnight at 20° C. in a closed vessel. Once IPC indicated free pentamer composition was below 3% (area % of the total reported) the reaction was considered complete. Filtration (using a P3 sintered glass funnel and 5 L Buchner flask) was required if there were any insoluble material present in reaction mixture. Contents of the reactor were freeze-dried in 2 Lyoguard trays. The shelf temperature was set at −0.5° C. for 16-20 h and then at 20° C. until dry. Freeze-dried product was dissolved in LE water (840 g) and divide equally between 6 centrifuge bottles. Acetone (630 g) was added to each container agitated for 15 minutes. Isopropanol (630 g per container) was added to each container and agitation continued for 20 min. Contents were centrifuged at 5300 RCF at 15° C., for 1 h. The supernatants were discarded and each pellet was dissolved in water by adding LE water (140 g) to each container and then agitating the mixture at ambient using an orbital shaker until the pellets dissolved. Acetone (630 g) was added to each container and agitated for 15 minutes. Isopropanol (630 g per container) was added to each container and agitation continued for 20 min. The contents were centrifuged at 5300 RCF at 15° C., for 1 h. The supernatants were discarded and each pellet was dissolved in water by adding LE water (100 g) followed by agitation at ambient. The solutions were transferred to a Lyoguard tray and bottles were rinsed with more LE water (66 g each) and the rinses were transferred to the same tray. The product was freeze-dried by setting the shelf temperature at −0.5° C. for 16-20 h and then at 20° C. until dry. Freeze-dried product was sampled for analytical and retention. The Lyoguard Tray was double-bagged, labelled and stored in the freezer (≤−15° C.). The potency of freeze-dried product was determined using qHNMR. This procedure afforded Crude Penta Dimer 17. Expected Yield: 26.1-35.5 g (61-83%).

The identity of the compound 17 was determined by $^1$H and $^{13}$C NMR using a 500 MHz instrument. A reference solution of t-butanol was prepared at 25 mg/mL in $D_2O$. Samples were prepared at 13 mg/mL in $D_2O$ and the reference solution is added to the sample. The composition of the final test sample was 10 mg/mL of the Penta Dimer and 5 mg/mL of t-butanol. The $^1$H and $^{13}$C spectra were acquired and integrated. The resulting chemical shifts were assigned by comparison to theoretical shifts. The $^1$H NMR and $^{13}$C NMR spectra are shown in FIGS. 1 and 2 respectively.

Example 5—Conversion of Crude Penta Dimer to Free Base Form

Amberlite FPA91 (1.46 kg; 40 g/g of Crude Penta Dimer—corrected for potency) was charged to a large column. A solution of 8 L of 1.0 M NaOH was prepared by adding NaOH (320 g) to LE water (8.00 kg) in a 10 L Schott Bottle. This solution was passed through Amberlite resin over a period of 1 hour. LE water (40.0 kg) was passed through the Amberlite resin. The resin was flushed with additional LE water (~10 kg aliquots) until a pH of <8.0 was attained in the flow-through. The crude Penta Dimer (49 g, PN0704), stored in a Lyoguard tray, was allowed to warm to ambient temperature. LE water (400 g) was added to the Lyoguard tray containing Crude Penta Dimer (49 g) and allowed to fully dissolve before transferring to a 1 L Schott bottle. The tray was rinsed with a further charge of LE water (200 g) and these washings were added to the Schott bottle contents. The Crude Penta Dimer solution was carefully poured onto the top of the resin. The 1 L Schott bottle was rinsed with LE water (200 g) and loaded this onto the resin. The Amberlite tap was opened to allow the Crude Penta Dimer solution to move slowly into the resin over ~5 min.

The tap was stopped and material left on the resin for ~10 min. LE water was poured onto the top of the resin. The tap was opened and eluted with LE water, collecting approximately 16 fractions of 500 mL. Each fraction was analyzed by TLC charring (10% $H_2SO_4$ in EtOH). All carbohydrate containing fractions were combined and filtered through a Millipore filter using a 0.2 µm nylon filter membrane. The solution was divided equally between 5-6 Lyoguard trays. The filtration vessel was rinsed with LE water (100 g) and divided between the trays. The material was freeze dried in the trays. The shelf temperature was set at −10° C. for 16-20 hr and then at +10° C. until the material was dry. LE water (150 g) was charged to all but one of the Lyoguard trays and transferred this into the one remaining tray containing dried material. Each of the empty trays was rinsed with a further charge of LE water (100 g) and this rinse volume was added to the final Lyoguard tray. The final Lyoguard tray was freeze dried. The shelf temperature was set at −10° C. for 16-20 hr and then at +10° C. until the materials dry. The product was sampled for analytical and retention. Dried material was transferred to HDPE or PP containers and stored at ≤−15° C. Expected yield: 31-34 g (86-94%).

TCEP reduction of the disulfide bond in the dimer is rapid and nearly stoichiometric. Use of a stoichiometric reduction with TCEP afforded approximately 2 equivalents of glucosamine pentasaccharide monomer. Specifically, the pentasaccharide dimer was dissolved in reaction buffer (50 mM HEPES buffer (pH 8.0)) containing 1 molar equivalent of TCEP. After 1 hour at ambient temperature, the reaction was analyzed by HPLC with CAD detection. Under these conditions, conversion to the penta-glucosamine monomer (peak at ~10 minutes) was nearly complete (penta glucosamine dimer peak at ~11.5 minutes). The remaining unannotated peaks were derived from the sample matrix. Based on the balanced chemical equation, the added TCEP was largely converted to TCEP oxide and any residual TCEP inhibited air oxidation back to the dimer prior to addition to the conjugation reaction. For simplicity, glucosamine pentasaccharide can be added based on input dimer and assuming >95% conversion to the monomer under these conditions.

The identity of the Penta Dimer was determined by $^1H$ and $^{13}C$ NMR using a 500 MHz instrument. A reference solution of t-butanol was prepared at 25 mg/mL in $D_2O$. Samples were prepared at 13 mg/mL in $D_2O$ and the reference solution was added to the sample. The composition of the final test sample was 10 mg/mL of the Penta Dimer and 5 mg/mL of t-butanol. The $^1H$ and $^{13}C$ spectra were acquired and integrated. The resulting chemical shifts are assigned by comparison to theoretical shifts. $^1H$ and $^{13}C$ NMR spectra are shown in FIGS. 1 and 2 respectively.

Example 6—Conversion to the Penta Saccharide Monomer of Example 4 with the TT of Example 1 to Provide for a Vaccine (Compound 18)

The TT monomer-linker intermediate of Example 2 was reacted with increasing concentrations of 4-70 pentameric glucosamine molar equivalents (2-35 pentasaccharide dimer molar equivalents) for 4 hours at ambient temperature. The crude conjugates from each titration point were purified by partitioning through a 30 kDa MWCO membrane. Each purified conjugate sample was analyzed for protein content, payload density by SEC-MALS and monomer/aggregate content by SEC HPLC. The data showed saturation of the payload density at ≥50 pentameric glucosamine equivalents. Based on the SEC HPLC analysis, the aggregate content increased as the pentasaccharide monomer charge was increased and appeared to reach steady state levels of an approximately 4% increase starting at 30 pentameric glucosamine equivalents. Based on these results, the pentasaccharide dimer charge selected for subsequent conjugation reactions was 25 molar equivalents, corresponding to a theoretical charge of 50 molar equivalents of pentameric glucosamine.

A series of three trial syntheses followed by a GMP synthesis of compound 18 were prepared as per above. Each of the resulting products was evaluated for potency (by ELISA assay) and payload density (molar ratio of pentameric glucosamine to tetanus toxoid).

The following table provides the results.

|  | Trial No. 1 | Trial No. 2 | Trial No. 3 | GMP Run |
|---|---|---|---|---|
| Payload Density of Compound 18 | 35 | 38 | 36 | 35 |
| Potency of Compound 18 | 94% | 101% | 87% | 98% |

These results evidence very high loading factors for the compounds.

Biological Examples

Example 8—Biofilm Inhibition

This example provides an illustrative approach to inhibiting biofilm formation prior to implantation of a prosthetic hip. Specifically, a first cohort of 10 mice (3 months old and weighing on average about 25 grams) is treated with an effective dose of a vaccine prepared as per Example 5 above. Approximately 1 month later, a blood draw is conducted on each mouse to confirm the presence of an effective antibody titer. A second control cohort of 10 mice (3 months old and weighing on average about 25 grams) is treated with a sterile aqueous solution identical to that of the first cohort with the exception that the aqueous solution does not contain the vaccine compound.

About 6 weeks after administration, both cohorts undergo surgery to introduce a prosthesis. Prior to introduction, the prosthesis is contaminated with S. aureus so as to initiate a bacterial infection. Both cohorts are maintained under identical conditions for approximately 2 months and then sacrificed. The prosthesis is then removed and evaluated for biofilm formation. It is contemplated that the first cohort will evidence little to no biofilm formation whereas the second cohort will evidence extensive biofilm formation.

What is claimed is:

1. A method for inhibiting biofilm formation in such subjects which method comprises:
   a) selecting an immune competent subject scheduled for implant surgery; and
   b) administering to said subject prior to surgery an effective amount of a vaccine represented by formula (I):

$$(A\text{-}B)_x\text{—}C \qquad (I)$$

where A comprises from 3 to 12 repeating saccharide β-(1→6)-glucosamine units or mixtures thereof having the formula:

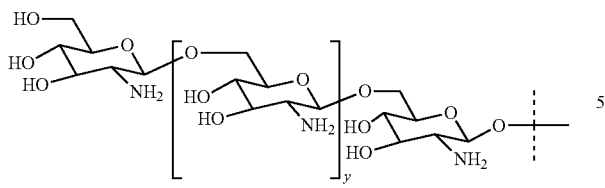

x represents the loading factor and is an integer from 10 to 40;

y is an integer from 1 to 10;

B is a linker group connecting A to C; and

C is an antigenic carrier; and c) maintaining said patient under conditions where endogenous antibodies against said oligo-β-(1→6)-glucosamine units are present provided that said antibodies are generated prior to implantation surgery so as inhibit formation of biofilm formation in said subject subsequent to said surgery.

2. The method of claim 1, wherein said vaccine is administered in a pharmaceutical composition.

3. The method of claim 2, wherein said pharmaceutical composition comprises an aqueous diluent and an adjuvant.

4. The method of claim 3, wherein said composition is sterile.

5. The method of claim 1, wherein y is a single integer.

6. The method of claim 1, wherein y is a mixture of integers.

7. The method of claim 1, wherein the carrier is a tetanus toxoid.

* * * * *